US008598127B2

(12) United States Patent
Han et al.

(10) Patent No.: US 8,598,127 B2
(45) Date of Patent: Dec. 3, 2013

(54) PEPTIDES FOR INHIBITING MDM2 FUNCTION

(75) Inventors: Kyou-Hoon Han, Daejeon (KR);
Seung-Wook Chi, Daejeon (KR);
Hyun-Jeong Kim, Seoul (KR);
Si-Hyung Lee, Daejeon (KR);
Min-Jung Ahn, Incheon (KR);
Do-Hyoung Kim, Daejeon (KR);
Jae-Sung Kim, Daejeon (KR); Shin-Ae Park, Seoul (KR)

(73) Assignee: Korea Research Institute of Bioscience & Biotechnology (KR)

( * ) Notice: Subject to any disclaimer, the term of this patent is extended or adjusted under 35 U.S.C. 154(b) by 1201 days.

(21) Appl. No.: 11/547,730

(22) PCT Filed: Dec. 29, 2004

(86) PCT No.: PCT/KR2004/003494
§ 371 (c)(1),
(2), (4) Date: Aug. 25, 2008

(87) PCT Pub. No.: WO2005/097820
PCT Pub. Date: Oct. 20, 2005

(65) Prior Publication Data
US 2009/0030181 A1 Jan. 29, 2009

(30) Foreign Application Priority Data
Apr. 6, 2004 (KR) .................. 10-2004-0023565

(51) Int. Cl.
*A61K 38/06* (2006.01)
*A61K 38/00* (2006.01)
(52) U.S. Cl.
USPC .......... 514/21.8; 514/1.1; 514/19.3; 514/19.6
(58) Field of Classification Search
None
See application file for complete search history.

(56) References Cited

U.S. PATENT DOCUMENTS 5,702,908 A 12/1997 Picksley et al.
5,858,976 A 1/1999 Burrell et al.

FOREIGN PATENT DOCUMENTS

WO WO 01/41788 * 6/2001

OTHER PUBLICATIONS

Leukemia from http://www.webmd.com/cancer/tc/leukemia-topic-overview, pp. 1-2. Accessed Aug. 6, 2009.*
Neuroblastoma from http://www.cancer.org/docroot/CRI/content/CRI_2_4_1X_What_is_neuroblastoma_31.asp, pp. 1-2. Accessed Aug. 6, 2009.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Lee, H. et al. Local Structure Elements in the Mostly Unstructured Transcriptional Activation Domain of Human p53. 2000, J. Biol Chem., 275, pp. 29426-29432.

* cited by examiner

*Primary Examiner* — Julie Ha
(74) *Attorney, Agent, or Firm* — Kohn & Associates PLLC

(57) ABSTRACT

Disclosed are peptides for inhibiting mdm2 (mouse double minute 2) and a pharmaceutical composition comprising the same.

3 Claims, 18 Drawing Sheets

FIG. 3

SEQ ID NO. 21  MEEPQSDPSVEPPLSQETFSDLWKLLPENNVLSPLPSQAMDDLMLSPDDIEQWFTEDPGPDEAPRMPEAAPPV

1. Gal 4D
2. Gal 4D p53 TAD(1-73)
3. p53 turn I L43A
4. p53 turn I L45A
5. p53 turn I L43A, L45A
6. p53 turn II L50A
7. p53 turn II W53A
8. p53 turn II F54A
9. p53 turn II L50A, W53A, F54A
10. p53 turn II L43A, L45A, L50A, W53A, F54A
11. p53 helix F19A
12. p53 helix W23A
13. p53 helix F19A, L22A, W23A, L26A Ala Turn II Turn II (49-54)

Trp Turn II

SEQUENCE LISTING

<160> NUMBER OF SEQ ID NOS: 43

<210> SEQ ID NO 1
<211> LENGTH: 73
<212> TYPE: PRT
<213> ORGANISM: Homo sapiens

<400> SEQUENCE: 1

Met Glu Glu Pro Gln Ser Asp Pro Ser Val Glu Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val
65                  70

<210> SEQ ID NO 2
<211> LENGTH: 25
<212> TYPE: DNA
<213> ORGANISM: Artificial Sequence
<220> FEATURE:
<223> OTHER INFORMATION: Forward primer

<400> SEQUENCE: 2
ggtcggatcc atggagccgc agtca                                         25

<210> SEQ ID NO 3
<211> LENGTH: 28
<212> TYPE: DNA
<213> ORGANISM: Artificial Sequence
<220> FEATURE:
<223> OTHER INFORMATION: Reverse primer

<400> SEQUENCE: 3
ggtgaagctt acacgggggg agcagcct                                      28

<210> SEQ ID NO 4
<211> LENGTH: 107
<212> TYPE: PRT
<213> ORGANISM: Homo sapiens

<400> SEQUENCE: 4

Asn Thr Asn Met Ser Val Pro Thr Asp Gly Ala Val Thr Thr Ser Gln
1               5                   10                  15

Ile Pro Ala Ser Glu Gln Glu Thr Leu Val Arg Pro Lys Pro Leu Leu
            20                  25                  30

Leu Lys Leu Leu Lys Ser Val Gly Ala Gln Lys Asp Thr Tyr Thr Met
            35                  40                  45

Lys Glu Val Leu Phe Tyr Leu Gly Gln Tyr Ile Met Thr Lys Arg Leu
    50                  55                  60

Tyr Asp Glu Lys Gln Gln His Ile Val Tyr Cys Ser Asn Asp Leu Leu
65                  70                  75                  80

Gly Asp Leu Phe Gly Val Pro Ser Phe Ser Val Lys Glu His Arg Lys
                85                  90                  95

Ile Tyr Thr Met Ile Tyr Arg Asn Leu Val Val
            100                 105

```
<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Ala Met Asp Asp Leu Met Leu Ser Pro Asp Asp Ile Glu Gln Trp Phe
1               5                   10                  15

Thr Glu Asp

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Asp Ile Glu Gln Trp Phe
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Asp Ala Glu Gln Ala Ala
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Ala Met Asp Asp Leu Met Leu Ser Pro Asp
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Asp Ile Glu Gln Trp Phe Thr Glu Asp
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Asp Ala Glu Gln Ala Ala Thr Glu Asp
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Asp Trp Glu Gln Trp Trp
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Asp Val Glu Gln Val Val
1               5

<210> SEQ ID NO 13
<211> LENGTH: 73
<212> TYPE: PRT
<213> ORGANISM: Artificial Sequence
<220> FEATURE:
<223> OTHER INFORMATION: Synthetic peptide

<400> SEQUENCE: 13

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Ala Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val
65                  70

<210> SEQ ID NO 14
<211> LENGTH: 73
<212> TYPE: PRT
<213> ORGANISM: Artificial Sequence
<220> FEATURE:
<223> OTHER INFORMATION: Synthetic peptide

<400> SEQUENCE: 14

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Ala Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val
65                  70

<210> SEQ ID NO 15
<211> LENGTH: 73
<212> TYPE: PRT
```

<213> ORGANISM: Artificial Sequence
<220> FEATURE:
<223> OTHER INFORMATION: Synthetic peptide

<400> SEQUENCE: 15

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Ala Met Ala Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val
65                  70

<210> SEQ ID NO 16
<211> LENGTH: 73
<212> TYPE: PRT
<213> ORGANISM: Artificial Sequence
<220> FEATURE:
<223> OTHER INFORMATION: Synthetic peptide

<400> SEQUENCE: 16

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ala Glu Gln Trp Phe Thr Glu Asp Pro Gly Pro Asp Glu Ala Pro
    50                  55                  60

Arg Met Pro Glu Ala Ala Pro Pro Val
65                  70

<210> SEQ ID NO 17
<211> LENGTH: 73
<212> TYPE: PRT
<213> ORGANISM: Artificial Sequence
<220> FEATURE:
<223> OTHER INFORMATION: Synthetic peptide

<400> SEQUENCE: 17

Met Glu Glu Pro Gln Ser Asp Pro Ser Val Glu Pro Pro Leu Ser Gln
1               5                   10                  15

Gln Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Ala Phe Thr Glu Asp Pro Gly Pro Asp Glu Ala Pro
    50                  55                  60

Arg Met Pro Glu Ala Ala Pro Pro Val
65                  70

<210> SEQ ID NO 18
<211> LENGTH: 73
<212> TYPE: PRT
<213> ORGANISM: Artificial Sequence
<220> FEATURE:
<223> OTHER INFORMATION: Synthetic peptide

<400> SEQUENCE: 18

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
            35                  40                  45

Asp Ile Glu Gln Trp Ala Thr Glu Asp Pro Gly Pro Asp Glu Ala Pro
        50                  55                  60

Arg Met Pro Glu Ala Ala Pro Pro Val
65                  70
```

<210> SEQ ID NO 19
<211> LENGTH: 73
<212> TYPE: PRT
<213> ORGANISM: Artificial Sequence
<220> FEATURE:
<223> OTHER INFORMATION: Synthetic peptide

<400> SEQUENCE: 19

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
            35                  40                  45

Asp Ala Glu Gln Ala Ala Thr Glu Asp Pro Gly Pro Asp Glu Ala Pro
        50                  55                  60

Arg Met Pro Glu Ala Ala Pro Pro Val
65                  70
```

<210> SEQ ID NO 20
<211> LENGTH: 73
<212> TYPE: PRT
<213> ORGANISM: Artificial Sequence
<220> FEATURE:
<223> OTHER INFORMATION: Synthetic peptide

<400> SEQUENCE: 20

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Ala Met Ala Ser Pro Asp
            35                  40                  45

Asp Ala Glu Gln Ala Ala Thr Glu Asp Pro Gly Pro Asp Glu Ala Pro
        50                  55                  60

Arg Met Pro Glu Ala Ala Pro Pro Val
65                  70
```

<210> SEQ ID NO 21
<211> LENGTH: 73
<212> TYPE: PRT
<213> ORGANISM: Artificial Sequence
<220> FEATURE:
<223> OTHER INFORMATION: Synthetic peptide

<400> SEQUENCE: 21

```
Met Glu Glu Pro Gln Ser Asp Pro Ser Val Glu Pro Pro Leu Ser Gln
1               5                   10                  15

Glu Thr Ala Ser Asp Ala Ala Lys Leu Ala Pro Glu Asn Asn Val Leu
```

```
                    20                  25                  30
Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val
65                  70

<210> SEQ ID NO 22
<211> LENGTH: 13
<212> TYPE: PRT
<213> ORGANISM: Human immunodeficiency virus type 1

<400> SEQUENCE: 22

Gly Arg Lys Lys Arg Arg Gln Arg Arg Arg Pro Pro Gln
1               5                   10

<210> SEQ ID NO 23
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 23

Asp Phe Glu Gln Trp Phe
1               5

<210> SEQ ID NO 24
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 24

Asp Trp Glu Gln Trp Phe
1               5

<210> SEQ ID NO 25
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 25

Asp Leu Glu Gln Trp Phe
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 26

Asp Phe Glu Gln Trp Trp
1               5

<210> SEQ ID NO 27
<211> LENGTH: 6
<212> TYPE: PRT
<213> ORGANISM: Artificial Sequence
<220> FEATURE:
```

```
<223> OTHER INFORMATION: synthetic peptide variant of p53

<400> SEQUENCE: 27

Asp Ile Glu Gln Trp Trp
1               5

<210> SEQ ID NO 28
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 28

Asp Leu Glu Gln Trp Trp
1               5

<210> SEQ ID NO 29
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 29

Asp Phe Glu Gln Trp Leu
1               5

<210> SEQ ID NO 30
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 30

Asp Trp Glu Gln Trp Leu
1               5

<210> SEQ ID NO 31
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 31

Asp Ile Glu Gln Trp Leu
1               5

<210> SEQ ID NO 32
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 32

Asp Leu Glu Gln Trp Leu
1               5

<210> SEQ ID NO 33
<211> LENGTH: 6
<212> TYPE: PRT
<213> ORGANISM: Artificial Sequence
<220> FEATURE:
<223> OTHER INFORMATION: synthetic peptide variant of p53
```

```
<400> SEQUENCE: 33

Asp Phe Glu Gln Trp Ile
1               5

<210> SEQ ID NO 34
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 34

Asp Trp Glu Gln Trp Ile
1               5

<210> SEQ ID NO 35
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 35

Asp Ile Glu Gln Trp Ile
1               5

<210> SEQ ID NO 36
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 36

Asp Leu Glu Gln Trp Ile
1               5

<210> SEQ ID NO 37
<211> LENGTH: 4
<212> TYPE: PRT
<213> ORGANISM: Artificial Sequence
<220> FEATURE:
<223> OTHER INFORMATION: synthetic peptide variant of p53

<400> SEQUENCE: 37

Leu Ser Pro Asp
1

<210> SEQ ID NO 38
<211> LENGTH: 5
<212> TYPE: PRT
<213> ORGANISM: Artificial Sequence
<220> FEATURE:
<223> OTHER INFORMATION: synthetic peptide variant of p53

<400> SEQUENCE: 38

Met Leu Ser Pro Asp
1               5

<210> SEQ ID NO 39
<211> LENGTH: 6
<212> TYPE: PRT
<213> ORGANISM: Artificial Sequence
<220> FEATURE:
<223> OTHER INFORMATION: synthetic peptide variant of p53

<400> SEQUENCE: 39
```

```
Leu Met Leu Ser Pro Asp
1               5

<210> SEQ ID NO 40
<211> LENGTH: 7
<212> TYPE: PRT
<213> ORGANISM: Artificial Sequence
<220> FEATURE:
<223> OTHER INFORMATION: synthetic peptide variant of p53

<400> SEQUENCE: 40

Asp Ile Met Leu Ser Pro Asp
1               5

<210> SEQ ID NO 41
<211> LENGTH: 8
<212> TYPE: PRT
<213> ORGANISM: Artificial Sequence
<220> FEATURE:
<223> OTHER INFORMATION: synthetic peptide variant of p53

<400> SEQUENCE: 41

Asp Asp Leu Met Leu Ser Pro Asp
1               5

<210> SEQ ID NO 42
<211> LENGTH: 9
<212> TYPE: PRT
<213> ORGANISM: Artificial Sequence
<220> FEATURE:
<223> OTHER INFORMATION: synthetic peptide variant of p53

<400> SEQUENCE: 42

Met Asp Asp Leu Met Leu Ser Pro Asp
1               5

<210> SEQ ID NO 43
<211> LENGTH: 19
<212> TYPE: PRT
<213> ORGANISM: Artificial Sequence
<220> FEATURE:
<223> OTHER INFORMATION: synthetic peptide variant of p53

<400> SEQUENCE: 43

Ala Met Asp Asp Leu Met Leu Ser Pro Asp Asp Ile Glu Gln Trp Phe
1               5                   10                  15

Thr Glu Asp
```

PEPTIDES FOR INHIBITING MDM2 FUNCTION

CROSS-REFERENCE TO RELATED APPLICATIONS

This is a National Phase Filing Under 35 U.S.C. 371, of International Application No. PCT/KR04/003494, filed Dec. 29, 2004, which claims priority to Korean Patent Application No. 10-2004-0023565, filed Apr. 6, 2004, both of which are incorporated herein by reference.

TECHNICAL FIELD

The present invention relates to peptides inhibiting mdm2 (mouse double minute 2) and a pharmaceutical composition comprising the same.

BACKGROUND ART p53 acts as a tumor suppressor protein, which participates in cell growth and apoptosis. Mutation of the p53 gene brings about inactivation of its translation product, which is a major cause of cancer. However, in some cases, although the p53 gene is present in the wild form, its protein product is often inactivated. One of such p53 inactivation mechanisms involves the overexpression of mdm2, a cellular oncogene. The p53 protein is autoregulated by a feedback loop mediated by the mdm2 protein, inhibiting p53 function through binding to the transcriptional activation domain (TAD) of p53, and the mdm2 protein binds to p53 and promotes p53 degradation through the ubiquitin-dependent pathway, thereby promoting the incidence of cancer (Oliner, J. D. et al. (1993) Nature 362, 857; Vassilev, L. T. et al. (2004) Science 303, 844-848; and Maki et al. (1999) J. Biol. Chem. 274, 1 6531).

Based on the finding that the mdm2 protein is amplified or overexpressed in many malignant tumors, leading to the inhibition of p53 function, the activation of the p53 pathway through the inhibition of mdm2 is becoming a new target for developing caner therapeutic agents.

One strategy to do this involves the development of low molecular weight agents capable of inhibiting the complex formation of p53 and mdm2. For example, piperazine derivatives useful in cancer therapy by inhibiting the interaction between mdm2 and p53 are disclosed in WO00/15657, U.S. Pat. No. 6,770,627, etc. WO03/051360 discloses the use of cis-imidazolines as mdm2 inhibitors, which are useful for the treatment of breast cancer, large intestine cancer, lung cancer, and the like. WO03/095625 discloses 1,4-benzodiazepines that act as inhibitors against the interaction between mdm2 and p53. WO03/106384A2 discloses boronic chalcone derivatives that inhibit mdm2 expression or complex formation with mdm2. Also, Stoll et al. describes chalcone derivatives inhibiting the binding of mdm2 to p53 (Stoll, R. et al. (2001) Biochemistry 40, 336-344).

Another strategy involves the development of mdm2-specific antisense oligonucleotides that inhibit mdm2 protein expression. Many publications, including WO99/49065 and WO99/10486, U.S. Pat. Nos. 6,013,786 and 6,238,921, and European Pat. No. 1 007 658, provide such antisense oligonucleotides.

In addition, other studies describe peptides that specifically bind to mdm2 and inhibit the binding of mdm2 to p53. The X-ray crystal structure of mdm2 bound to the p53 TAD peptide reveals that only a helix formed by residues 18-26 of the p53 TAD binds to mdm2 (Kussie, R. H. et al., (1996) Science 274, 948-953). Since then, based on this X-ray crystal structure, many studies have been focused on the p53 α-helix. For example, WO96/02642 provides a peptide encompassing amino acid residues 19-23 of the p53 α-helix. U.S. Pat. No. 5,702,908 provides a peptide encompassing amino acid residues 18-23 of the p53 α-helix. WO98/476525 provides a peptide encompassing amino acid residues 19-23 of the p53 α-helix. WO98/01467 provides a peptide encompassing amino acid residues 19-26 of the p53 α-helix. U.S. Pat. No. 5,858,976 provides a peptide encompassing amino acid residues 14-41 of the p53 α-helix. These peptides, consisting of amino acid residues of the p53 α-helix region, are characterized by inhibiting mdm2.

The present inventors, in a previous study, reported that, unlike the previous view that the p53 TAD is unstructured, the p53 TAD has local secondary structures such as an α-helix and a turn even in the state of being unbound to mdm2 (Lee, H. et al. (2000) J. Biol. Chem. 275, 29426-29432).

To date, all of studies involving peptides inhibiting the binding of mdm2 and p53 have been focused only on the helix region of the p53 TAD, based on the X-ray crystal structure of the complex of mdm2 with the p53 TAD peptide. Also, there is no research describing substantial binding between mdm2 and a turn that is another secondary structure of the p53 TAD, and turn-derived peptides inhibiting the binding of mdm2 and p53.

In this regard, the intensive and thorough research into the effect of the turns of the p53 TAD on mdm2 binding thereto by chemical shift perturbation experiments using nuclear magnetic resonance (NMR) spectroscopy resulted in the finding that the turns as well as the helix participate directly in the binding of the p53 TAD to mdm2, and in particular, a region encompassing amino acid residues 49-54, forming turn II, is most critical for the binding to mdm2. The finding further includes that, when a peptide sequence corresponding to this region or a derivative thereof is administered to cancer cells, it inhibits the binding of mdm2 to p53 and activates the p53 pathway to induce apoptosis, thereby leading to the present invention providing peptides for inhibiting mdm2.

SUMMARY OF THE INVENTION

It is therefore an object of the present invention to provide a peptide inhibiting mdm2, or a pharmaceutically acceptable salt thereof.

It is another object of the present invention to provide a composition for inhibiting mdm2-mediated degradation, comprising the peptide.

It is a further object of the present invention to provide a method of inhibiting mdm2-mediated degradation, based on administering the peptide.

BRIEF DESCRIPTION OF THE DRAWINGS

FIG. 3 shows NMR peaks that disappeared during the titration, mentioned in FIG. 2, of $^{15}$N-p53 TAD(1-73) with mdm2(3-109). NMR peaks that disappeared and peaks that weakened in peak size are indicated in black and white circles, respectively.

BEST MODE FOR CARRYING OUT THE INVENTION

Figure 1:
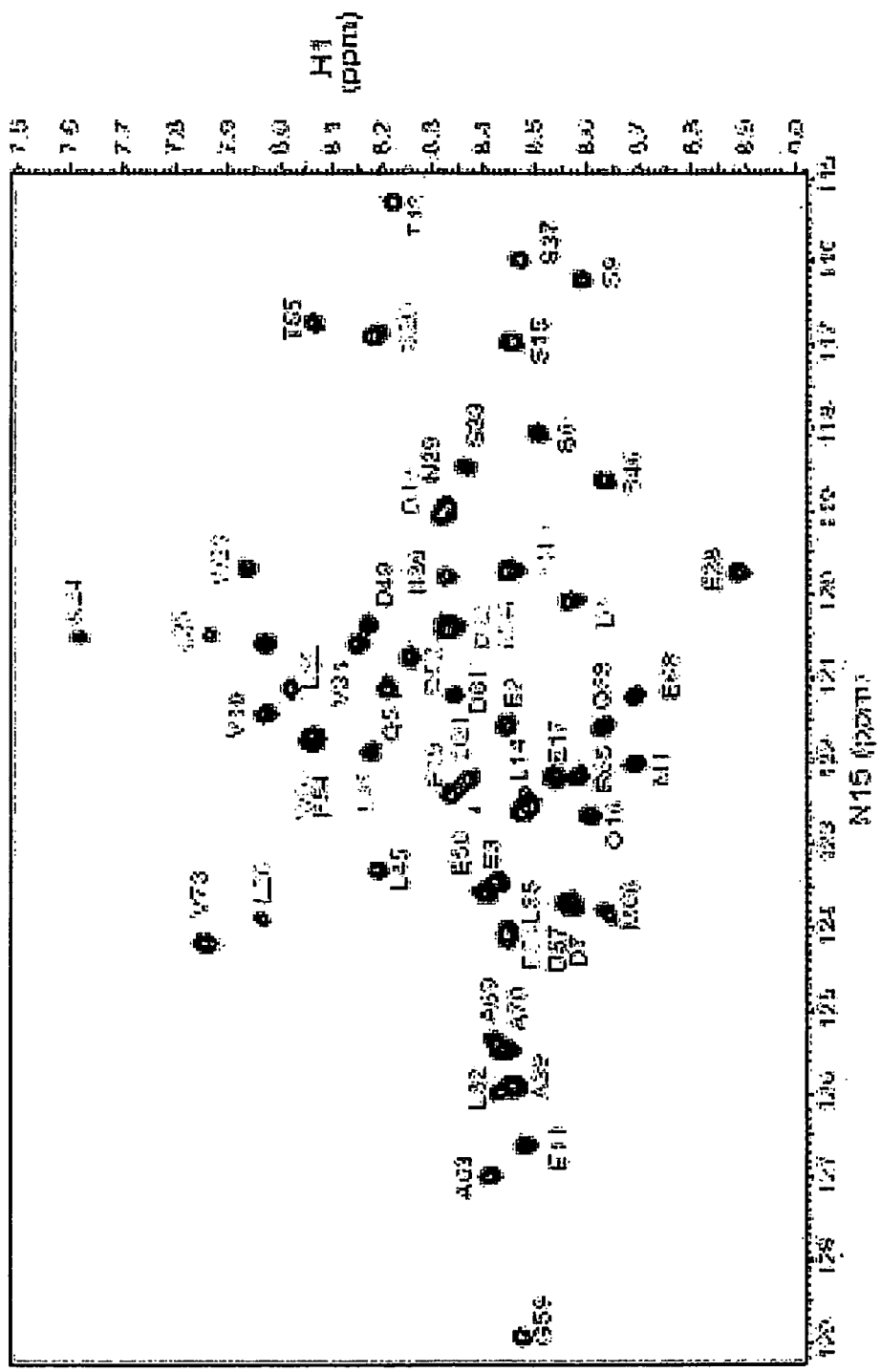
FIG. 1 is a $^{15}$N—$^{1}$H HSQC spectrum of $^{15}$N-p53 TAD(1-73) in a free state recorded at 0.4 mM of $^{15}$N-p53 TAD(1-73) and 5° C. NMR peaks for residues (Thr18-Leu26) forming an α-helix and residues (Met40-Met44 and Asp48-Trp53) forming two turns are indicated in red and green, respectively, and peaks that disappeared during titration with mdm2 (3-109) and unchanged peaks are indicated in blue and black, respectively.

In one aspect, the present invention provides a peptide for inhibiting mdm2, comprising an amino acid sequence represented by Formula 1, or a pharmaceutically acceptable salt thereof.

$X^1-Z^1-X^2-X^3-Z^2-Z^3$ [Formula 1]

wherein, $X^1$, $X^2$ and $X^3$ are identical or different, each indicating one amino acid selected from among natural amino acids and non-natural amino acids; and $Z^1$, $Z^2$ and $Z^3$ are identical or different, each indicating one amino acid selected from the group consisting of phenylalanine, leucine, isoleucine, alanine, valine, proline, tyrosine, histidine, methionine, trytophane, and non-natural amino acid derivatives thereof.

The term "peptide", as used herein, is a polymer that consists of amino acids linked with each other by amide bonds (or peptide bonds). With respect to the objects of the present invention, the term means a peptide that specifically binds to mdm2 and inhibits mdm2. The peptide, which is a peptide having an amino acid sequence corresponding to a region forming the turn II of the p53 TAD binding to mdm2 or a sequence having an activity corresponding thereto, serves as a competitive substrate for a protein binding to mdm2, such as p53, and inhibits the binding of mdm2 to a variety of substrate proteins. Preferably, the peptide is a peptide inhibiting the binding of mdm2 and p53.

The present inventors found that the turns as well as the helix of p53 participate in the binding to mdm2, and, in particular, chemical shift perturbation experiments reveled that a p53 TAD(49-54) peptide plays a more potent role in the binding to mdm2 than another p53 TAD(39-48) peptide. The specific binding of the p53 TAD(49-54) peptide and an mdm2 (3-109) protein was confirmed by BIAcore analysis, and NMR spectroscopy revealed that the p53 TAD(49-54) peptide forms a helix structure in its state of being bound to mdm2 (3-109).

The present peptide, having the amino acid sequence of Formula 1, may have additional amino acid sequences at the front of its N-terminal end and at the rear of its C-terminal end. The length substantially binding to mdm2 is not particularly limited, but, preferably, the peptide may further include an amino acid sequence of 0 to 10 residues at the front of its N-terminal end and an amino acid sequence of 0 to 3 residues at the rear of its C-terminal end.

Thus, in another aspect, the present invention provides a peptide binding to mdm2 or a pharmaceutically acceptable salt thereof, comprising an amino acid sequence of Formula 1, an amino acid sequence of 0 to 10 residues at the front of an N-terminal end thereof and an amino acid sequence of 0 to 3 residues at the rear of a C-terminal end thereof.

In the amino acid sequence of Formula 1, the natural amino acids are selected from the group consisting of aspartic acid, alanine, arginine, asparagine, cysteine, glutamic acid, glutamine, glycine, histidine, leucine, lysine, isoleucine, methionine, phenylalanine, proline, serine, threonine, trytophane, tyrosine and valine. The non-natural amino acids are preferably selected from the group consisting of alpha-aminoisobutyric acid (Aib), 1-amino-cyclopropanecarboxylic acid (Ac3c), norleucine (Nie), methylglycine (MeGly), 4-phosphonomethyl phenylalanine (Pmp), 5-methyl tryptophane (5-Me-Trp), 6-methyl tryptophane (6-Me-Trp), 6-chlorotryptophane (6-Cl-Trp) and 6-fluorotryptophane (6-F-Trp). Thus, the amino acid residues $X^1$, $X^2$ and $X^3$ may be selected from the group consisting of aspartic acid, alanine, arginine, asparagine, cysteine, glutamic acid, glutamine, glycine, histidine, leucine, lysine, isoleucine, methionine, phenylalanine, proline, serine, threonine, trytophane, tyrosine, valine, alpha-aminoisobutyric acid, 1-amino-cyclopropanecarboxylic acid, norleucine, methylglycine, 4-phosphonomethyl phenylalanine, 5-methyl tryptophane, 6-methyl tryptophane, 6-chlorotryptophane and 6-fluorotryptophane. More preferably, $X^1$ is aspartic acid (Asp: D), $X^2$ is glutamic acid (Glu: E), and $X^3$ is glutamine (Gln: Q).

The non-natural amino acid derivative for the amino acid residues $Z^1$, $Z^2$ and $Z^3$ may be Nle, 5-Me-Trp, 6-Me-Trp, 6-Cl-Trp or 6-F-Trp. Thus, the amino acid residues $Z^1$, $Z^2$ and $Z^3$ may be preferably selected from the group consisting of phenylalanine, leucine, isoleucine, alanine, valine, proline, tyrosine, histidine, methionine, trytophane, norleucine, 5-methyl tryptophane, 6-methyl tryptophane, 6-chlorotryptophane and 6-fluorotryptophane. Preferably, $Z^1$, $Z^2$ and $Z^3$ are phenylalanine, leucine, isoleucine, alanine, valine, proline, tyrosine, histidine, methionine, trytophane, or norleucine. More preferably, $Z^1$, $Z^2$ and $Z^3$ are trytophane, phenylalanine, leucine, isoleucine, or norleucine. Even more preferably, $Z^2$ is trytophane (Trp: W), $Z^1$ is isoleucine (Ile: I) or trytophane, and $Z^3$ is phenylalanine (Phe: F) or trytophane.

In a preferred embodiment, the X.sup.1-Z.sup.1-X.sup.2-X.sup.3-Z.sup.2-Z.sup.3 peptide is DFEQWF (SEQ ID NO. 23), DWEQWF (SEQ ID NO. 24), DIEQWF (SEQ ID NO. 6), DLEQWF (SEQ ID NO. 25), DFEQWW (SEQ ID NO. 26), DWEQWW (SEQ ID NO. 11), DIEQWW (SEQ ID NO. 27), DLEQWW (SEQ ID NO. 28), DFEQWL (SEQ ID NO. 29), DWEQWL (SEQ ID NO. 30), DIEQWL (SEQ ID NO. 31), DLEQWL (SEQ ID NO. 32), DFEQWI (SEQ ID NO. 33), DWEQWI (SEQ ID NO. 34), DIEQWI (SEQ ID NO. 35) or DLEQWI (SEQ ID NO. 36). In a more preferred embodiment, the peptide is DWEQWW (SEQ ID NO. 11) or DIEQWF (SEQ ID NO. 6).

Amino acids of the peptide of the present invention may be an L-form or a D-form. In the peptide, according to the intended use, a specific atom or atomic group may be a derivative replaced with a hydroxyl group, a methyl group, or the like, a carboxyl group at a C-terminal end may be replaced with carboxylamide, ester, or the like, and an amino group at an N-terminal end may be replaced with an acetyl group, hydrogen, or the like.

The term "an amino acid sequence of 0 to 10 residues at the front of an N-terminal end", as used herein, refers to an amino acid sequence of 0, 1, 2, 3, 4, 5, 6, 7, 8, 9 or 10 residues, which is located to the left of the X.sup.1 amino acid residue of the peptide, and preferably includes a sequence of D, PD, SPD, LSPD (SEQ ID NO. 37), MLSPD (SEQ ID NO. 38), LMLSPD (SEQ ID NO. 39), DIMLSPD (SEQ ID NO. 40), DDLMLSPD (SEQ ID NO. 41), MDDLMLSPD (SEQ ID NO. 42) or AMDDLMLSPD (SEQ ID NO. 8). The term "an amino acid sequence of 0 to 3 residues at the rear of a C-terminal end", as used herein, refers to an amino acid sequence of 0, 1, 2 or 3 residues, which is located to the right of the Z.sup.3 amino acid residue of the peptide, and preferably includes a sequence of T, TE or TED.

In addition, the present peptide may further include a targeting sequence, a tag, a labeled residue) or an additional amino acid sequence designed with a specific aim to increase the half-life or stability of the peptide. Also, the present peptide may be linked to a coupling partner, such as effectors, drugs, prodrugs, toxins, peptides and vehicles. In a detailed aspect of the present invention, a cell permeable peptide consisting of 48-60 amino acid residues of HIV-1 Tat protein was linked to an N-terminal end of an mdm2-bound peptide of the present invention.

The peptide may be prepared using a genetic recombination technique and a protein expression system, or by in vitro synthesis using a peptide synthesizer.

The pharmaceutically acceptable salt of the present peptide may be formed by the addition of inorganic acids (e.g., hydrochloric acid, hydrobromic acid, phosphoric acid, nitric acid, sulfuric acid, etc.), organic carboxylic acids (e.g., acetic acid, haloacetic acid such as trifluoroacetic acid, propionic acid, maleic acid, succinic acid, malic acid, citric acid, tartaric acid, salicylic acid), and organic sulfonic acid (e.g., methane sulfonic acid, ρ-toluene sulfonic acid), including acidic sugars (e.g., glucuronic acid, galacturonic acid, gluconic acid, ascorbic acid), acidic polysaccharides (e.g., hyaluronic acid, chondroitin sulfate, alginic acid), and sugar sulfonic esters, such as chondroitin sulfate.

In a further aspect, the present invention provides a composition for inhibiting mdm2-mediated degradation, comprising the peptide.

Mdm2 is known to promote the degradation of the p53 protein via a ubiquitin-dependent pathway. When cancer cells or virus-infected cells are treated with a composition comprising the peptide of the present invention, mdm2-mediated p53 degradation is inhibited, and apoptosis is induced.

In a preferred aspect of the present invention, an alanine-substituted peptide having an amino acid sequence of DAEQAA (SEQ ID NO. 7), used as a negative control, is unable to induce apoptosis in cancer cells. In contrast, a native peptide, specifically binding to mdm2 and having an amino acid sequence of DIEQWF (SEQ ID NO. 6), effectively induces apoptosis. In particular, a substituted peptide having an amino acid sequence of DWEQWW (SEQ ID NO. 11) has greatly higher activity in inducing apoptosis than the native DIEQWF (SEQ ID NO. 6) peptide.

Thus, the present invention provides an anticancer or antiviral composition for inhibiting mdm2-mediated degradation and promoting p53-dependent apoptosis, and more preferably a composition for preventing or treating cancer caused by mdm2 amplification or everexpression.

The amplification and overexpression of mdm2 are found in many types of cancer regardless of p53 mutation. For example, increased transcription levels of mdm2 are observed in leukemia, lymphomas, and the like. Mdm2 is amplified in esophageal carcinomas, neuroblastoma, soft tissue tumors, and the like. Soft tissue tumors include Ewing's sarcoma, leiomysarcoma, lipomas, liposarcoma, malignant fibrous histiocytomas, malignant schwannomas, and the like (Jamil Momand et al., (1998) Nucleic Acids Research, 26, 3453-3459).

Therefore, the present composition may be preferably used for preventing or treating leukemia, lymphomas, esophageal carcinomas, neuroblastoma and soft tissue tumors.

The present composition may include one or more kinds of the above peptides, wherein the peptides may include sugar chain compounds, lipid compounds, nucleic acid compounds, and other types of peptides or proteins. Lipid compounds are exemplified by dipalmitoylphosphatidylcholine (DPPC), palmitoyloleylphosphatidylglycerol (POPG), phosphatidylglycerol (PG), $C_{18}$ saturated fatty acids, $C_{16}$ unsaturated fatty acids, and $C_{18}$ unsaturated fatty acids.

The present composition comprises an acceptable carrier and is formulated into a suitable pharmaceutical preparation according to administration methods. Suitable pharmaceutical preparations according to administration methods are known, and typically, may include surfactants facilitating transport of drugs across a membrane. Such surfactants include derivatives of steroids, cationic lipids such as N-[1-(2,3-dioleyloxy)propyl]-N,N,N-trimethylammonium chloride (DOTMA), and cholesterol hemisuccinate.

A composition comprising the above peptide as an effective ingredient may be used in general medicament forms. Formulations for parenteral administration may include sterile aqueous solutions, non-aqueous solutions, suspensions, emulsions, lyophilized preparations, and suppositories. Nonaqueous solutions and suspensions may contain propylene glycol, polyethylene glycol, vegetable oils such as olive oil, and injectable esters such as ethyl oleate. As a base of suppositories, witepsol, macrogol, tween 61, cacao oil, laurin oil and glycerinated gelatin may be used. Also, the peptides may be used in combination with several pharmaceutically acceptable carriers, such as physiological saline or organic solvents. In order to increase the stability or absorption of the peptides, carbohydrates, such as glucose, sucrose or dextrin, antioxidants, such as ascorbic acid or glutathione, chelating agents, low molecular weight proteins or other stabilizers may be used.

In addition, the present composition may include a nucleic acid encoding the peptide to produce the peptide in cells.

In still another aspect, the present invention provides a method of inhibiting mdm2-mediated degradation, based on administering the peptide.

Preferably, there is provided a method of preventing or treating cancer or viral diseases by inhibiting the binding of mdm2 and p53, and more preferably, a method of preventing or treating leukemia, lymphomas, esophageal carcinomas, neuroblastoma, and soft tissue tumors, including Ewing's sarcoma, leiomyosarcoma, lipomas, liposarcoma, malignant fibrous histiocytomas, and malignant schwannomas.

The present composition is formulated into a suitable pharmaceutical preparation along with a pharmaceutically acceptable carrier and administered via a variety of routes. "Administration" means to introduce a certain substance into a patient by any proper method. The composition may be administered via any of the common routes, as long as it is able to reach a desired tissue. The present composition may be administered intraperitoneally, intravenously, intramuscularly, subcutaneously, intradermally, orally, topically, intranasally, intrapulmonarily and intrarectally, but the present invention is not limited to these examples. However, since a peptide is digested upon oral administration, a composition for oral administration is preferably prepared in such a way that an active drug is coated or formulated to be protected from degradation in the stomach. Also, the pharmaceutical composition may be administered by means of a certain device capable of transporting an active substance to target cells. Preferred administration modes and formulations are intravenous injections, subcutaneous injections, intradermal injections, intramuscular injections, dropping injections, etc. Injectable preparations may be prepared using physiological saline, aqueous solutions such as Ringer's solution, and nonaqueous solutions, such as vegetable oils, long chain fatty acid esters (e.g., ethyl oleate, etc.) and alcohols (e.g., ethanol, bezylalcohol, propylene glycol, glycerin, etc.), and may include pharmaceutical carriers, which are exemplified by stabilizers for deterioration prevention (e.g., ascorbic acid, sodium hydrosulphite, sodium pyrosulfite, BHA, tocopherol, EDTA, etc.), emulsifying agents, buffering agents for pH control, and preservatives for inhibiting microbial growth (e.g., phenylmercuric nitrate, thimerosal, benzalkonium chloride, phenol, cresol, benzylalcohol, etc.).

The present composition may be administered in a pharmaceutically effective amount. The term "pharmaceutically effective amount" refers to an amount sufficient for displaying a therapeutic effect but not causing side effects, and may be easily determined by those skilled in the art according to factors known in the medical field, including the type of illness, the patient's age, weight, health state, gender and sensitivity to drugs, administration routes, administration methods, administration frequency, treatment duration, and drugs used in combination or simultaneously. Generally, an active substance may be administered in a dose from about 0.01 mg/kg/day to 1000 mg/kg/day. For oral administration, a dose ranging from 50 to 500 mg/kg may be suitable, and the dose may be administered one or more times per day.

A better understanding of the present invention may be obtained through the following examples which are set forth to illustrate, but are not to be construed as the limits of the present invention.

EXAMPLE 1

Production of Human p53 TAD and mdm2 Protein

The p53 TAD domain (SEQ ID NO. 1) corresponding to residues 1-73 of the TAD of human p53 was cloned (Lee, H. et al. (2000) J. Biol. Chem. 275, 29426-29432). Oligonucleotides for a forward primer of SEQ ID NO. 2 and a reverse primer of SEQ ID NO. 3 were synthesized. Using the primers, PCR was carried out, and the PCR product was inserted into an *E. coli* expression vector pGEX-2T (Stratagene) using BamHI and HindIII sites.

```
Forward primer:
5'-GGTCGGATCCATGGAGCCGCAGTCA-3'        (SEQ ID NO. 2)

Reverse primer:
3'-GGTGAAGCTTACACGGGGGGAGCAGCCTC-5'    (SEQ ID NO. 3)
```

The p53 TAD(1-73) contained glycine and serine derived from the vector at its N-terminal end, and was expressed as a protein fused with glutathione transferase (GST) at its N-terminal end, GST-p53 TAD(1-73). For overexpression of GST-p53 TAD(1-73), transformed BL21(DE3) *E. coli* cells were cultured in M9 minimum medium at 37° C. When the culture reached an $OD_{600}$ value of 0.7, IPTG (isopropyl thio-β-D-thiogalactopyranoside) was added to the medium at a final concentration of 0.6 mM, and the cells were further cultured for 4 hrs. The M9 minimum medium used for $^{15}$N-isotope labeling was supplemented with 1 mg/ml $^{15}NH_4Cl$, 0.4% glucose, 2 mg/l biotin, 2 mg/l thiamine, 1 mM magnesium sulfate ($MgSO_4$), 0.1 mM calcium chloride ($CaCl_2$), and 0.05 mg/ml ampicillin. The cultured cells were collected by centrifugation and lysed in a buffer solution (50 mM sodium phosphate (pH 7.8), 1 mM PMSF, 10 mM β-mercaptoethanol) by ultrasonication. The GST-p53 TAD(1-73) fusion protein was bound to a glutathione sepharose affinity resin (Amersham Pharmacia Biotech) and cleaved with thrombin (Roche Molecular Biochemicals) to release the p53 TAD(1-73). The p53 TAD(1-73) was then purified using a SOURCE 15Q FPLC ion column and a Vydac C18 HPLC column.

Also, the human mdm2 N-terminal domain (SEQ ID NO. 4), corresponding to 3-109 residues in a pLM1 vector, was overexpressed in BL21(DE3) *E. coli* cells (Uesugi M. et al. (1999) Proc. Natl. Acad. Sci. U.S.A. 96, 14801-1480). Transformed *E. coli* cells were cultured in LB medium at 37° C. When the culture reached an $OD_{600}$ value of 0.6, IPTG was added to the medium at a final concentration of 0.4 mM, and the cells were further cultured at 30° C. for 4 hrs. The cultured cells were collected by centrifugation and lysed in a buffer solution (50 mM Tris HCl (pH 7.5), 0.4 M NaCl, 1 mM PMSF, 10 mM β-mercaptoethanol) by ultrasonication. After centrifugation, ammonium sulfate was added to the supernatant to precipitate proteins. The precipitated proteins were dissolved in a buffer solution (50 mM Tris-HCl (pH 7.5), 0.4 M NaCl, 1 mM PMSF, 10 mM β-mercaptoethanol), and were purified using SP-sepharose and Q-sepharose column chromatography and Hiprep 26/60 Sephacryl S-200 FPLC column (Pharmacia Biotech). For purification of $^{15}$N-labeled mdm2(3-109) and $^{15}$N, $^{13}$C-labeled mdm2(3-109) proteins, cells were cultured in M9 minimum medium supplemented with $^{15}$NH4Cl or $^{13}$C-glucose and $^{15}$NH$_4$Cl, and, after IPTG was added to the medium, the cells were further cultured at 20° C. for 16 hrs. Then, expressed proteins were purified as described above.

EXAMPLE 2

Synthesis of p53 Fragment Peptides p53 fragment peptides were synthesized by a solid-phase method using an APEX 348W peptide synthesizer (Advanced Chemtech). The synthesized peptides were as follows:

```
p53 (39-57)
AMDDLMLSPDDIEQWFTED;        (SEQ ID NO. 5)

p53 (49-54)
DIEQWF;                     (SEQ ID NO. 6)
```

Ala-substituted peptide having I50A/W53A/F54A substitutions relative to the native p53(49-54) peptide—DAEQAA (SEQ ID NO. 7);

```
p53 (39-48)
AMDDLMLSPD;                 (SEQ ID NO. 8)

p53 (49-57)
DIEQWFTED;                  (SEQ ID NO. 9)
```

Ala-substituted peptide having I50A/W53A/F54A substitutions relative to the native p53(49-57) peptide—DAEQAATED (SEQ ID NO. 10);

Trp-substituted peptide having I50W/F54W substitutions in the native p53 (49-54) peptide—DWEQWW (SEQ ID NO. 11); and Val-substituted peptide having I50V/W53V/F54V substitutions relative to the native p53(49-54) peptide—DVEQVV (SEQ ID NO. 12).

The C-terminal end of all of the synthesized p53 fragment peptides was amidated and purified with a Vydac C18 HPLC column after being synthesized. The finally purified fragment peptides were subjected to MALDI-TOF mass spectrometry to determine their molecular weights.

EXAMPLE 3

NMR Spectroscopy

All NMR data were measured using a Varian Unity INOVA 600 MHz NMR spectrometer at 5° C. and 25° C. $^{15}$N—$^1$H HSQC (heteronuclear single quantum coherence spectroscopy) spectra were collected with spectral widths of 8000 Hz in the $^1$H dimension and 1800 Hz in the $^{15}$N dimension, and with 1024 data points in the t2 domain and 256 data points in the t1 domain.

Chemical shift assignment studies for a mdm2(3-109) protein in a free and bound states were performed using three-dimensional (3D) HNCA and HNCOCA experiments of $^{15}$N, $^{13}$C-mdm2(3-109), and $^{15}$N-edited TOCSY and $^{15}$N-edited NOESY (mixing time=150 ms) experiments of $^{15}$N-mdm2 (3-109), all of which were carried out at 25° C. $^{15}$N-mdm2 (3-109) and $^{15}$N, $^{13}$C-mdm2(3-109), dissolved in a buffer solution (25 mM Tris HCl (pH 7.5), 150 mM NaCl, 2 mM DTT, 0.1 mM PMSF, 0.1 mM EDTA, 0.1 mM benzamidine, 0.02% NaN$_3$), were subjected to 3D NMR experiments in which mdm2(3-109) in a free state was used at 0.4 mM. A 3D NMR experiment for mdm2(3-109) in a bound state was performed after p53 TAD(1-73) was added at a molar ratio of 1:1 (p53 TAD(1-73):the protein).

To analyze the structure of the p53 TAD(39-57) fragment peptide, 2D NMR experiments were performed for p53 TAD (39-57) dissolved in 80% methanol at 10° C., 4 mM of p53 TAD(39-57) and pH 6.1. Also, TRNOE experiments were performed to identify the structure of p53 TAD(39-57) in complex with mdm2(3-109) in H$_2$O. TRNOE spectra were recorded at 0.1 mM of mdm2(3-109), 2 mM of p53 TAD(39-57), 10° C. and a mixing time of 100 ms, using a solvent consisting of 25 mM Tris-HCl (pH 7.5) and 150 mM NaCl.

Sequence-specific resonance assignments were performed with TOCSY (Griesinger, C. et al. (1988) J. Am. Chem. Soc. 110, 7870-7872), NOESY (mixing time=200 ms) and ROESY experiments. $^3J_{HNH\alpha}$ coupling constants were measured with DQF-COSY experiments (Rance, M. et al. (1987) Biochem. Biophys. Res. Commun. 117, 479-485). These 2D NMR spectra were collected with spectral widths of 8000 Hz in both dimensions and with 2048 data points in the t2 domain and 256 data points in the t1 domain. All NMR data were processed and analyzed on a Sun SPARCstation using Varian Vnmr and nmrPipe/nmrDraw software (Delaglio, F. et al. (1995) J. Biomol. NMR. 6, 277-293).

EXAMPLE 4

Chemical Shift Perturbation Experiments

2D $^{15}$N—$^1$H HSQC spectra were collected for the $^{15}$N-labeled p53 TAD(1-73) protein, dissolved in a buffer solution of 50 mM sodium acetate-d3 (pH 6.3) and 50 mM NaCl (90% H$_2$O/10% D$_2$O), at 0.4 mM of $^{15}$N-p53 TAD(1-73) and at 5° C. Then, the mdm2(3-109) protein was added to the $^{15}$N-p53 TAD(1-73) protein while its amount was gradually increased, and, during the titration, $^{15}$N—$^1$H HSQC spectra of $^{15}$N-p53 TAD(1-73) were collected at various $^{15}$N-p53 TAD(1-73): mdm2(3-109) molar ratios of 1:0, 1:0.3, 1:0.6, 1:1 and 1:2.

Also, $^{15}$N—$^1$H HSQC spectra were collected for the $^{15}$N-labeled mdm2(3-109) protein, dissolved in a buffer solution of 25 mM Tris HCl (pH 7.5), 150 mM NaCl, 2 mM DTT, 0.1 mM PMSF, 0.1 mM EDTA, 0.1 mM benzamidine and 0.02% NaN$_3$, at 0.2 mM of $^{15}$N-mdm2(3-109) and 25° C. Then, p53 TAD(1-73) or the p53 fragment peptides prepared in Example 2 were added to the $^{15}$N-mdm2(3-109) protein. During titration, $^{15}$N-1H HSQC spectra of $^{15}$N-mdm2(3-109) in a bound state were collected at $^{15}$N-mdm2(3-109):p53 TAD molar ratios of 1:0, 1:0.2, 1:0.4, 1:0.6, 1:1 and 1:1.7 for the p53 TAD(1-73), and 1:0, 1:0.5, 1:1, 1:3 and 1:6 for the p53 TAD fragment peptides.

EXAMPLE 5

BIAcore Experiments

BIAcore experiments were carried out using a BIAcore 2000 instrument. A CM5 sensor chip (Pharmacia Biosensor, Sweden) was installed in the instrument and washed with HBS buffer (10 mM Hepes-NaOH, pH 7.4, 150 mM NaCl, 1 mM EDTA, 0.005% Tween 20), and its carboxymethyl dextran surface was activated by injection with 100 µl of an EDC/NHS mixture. 150 µl of mdm2(3-109), dissolved in a concentration of 1 mg/ml in a buffer of 25 mM sodium acetate (pH 4.5) and 150 mM NaCl, was injected over the activated CM5 sensor chip and immobilized thereonto by amine coupling. After coupling, 1 M ethanolamine was passed over the chip to inactivate the remaining activated carboxyl groups unreacted with the mdm2(3-109) protein, and 10 mM glycine (pH 2.0) was injected over the chip to remove protein molecules unbound to the sensor chip. Then, 60 μl of the p53(49-54) peptide in the HBS buffer was injected over the sensor chip in various concentrations (50 μM; 25 μM, 12.5 μM, 6.25 μM, 3.125 μM and 1.5625 μM), and sensorgram data were collected during binding and dissociation according to time. 10 μl of 1 M sodium chloride was injected every time after the peptide injection to dissociate bound peptides. Flow rates were 10 μl/min for activation and inactivation of the sensor chip and immobilization, and 20 μl/min for binding and removal of sodium chloride. Sensorgram data in an equilibrium state were plotted and fitted according to concentrations to calculate a dissociation equilibrium constant (Kd) (van Holde, K. E. et al. (1998) Principles of Physical Biochemistry).

EXAMPLE 6

Evaluation of Transcription Activity of p53 TAD Mutants p53 TAD mutants alanine-substituted for hydrophobic residues present at the helix and turn regions of p53 were cloned. Mutants for the turn regions of p53 were an L43A mutant of SEQ ID NO. 13, an L45A mutant of SEQ ID NO. 14, a L43A/L45A mutant of SEQ ID NO. 15, an I50A mutant of SEQ ID NO. 16, a W53A mutant of SEQ ID NO. 17, an F54A mutant of SEQ ID NO. 18, an I50A/W53A/F54A mutant of SEQ ID NO. 19, and an L43A/L45A/I50A/W53A/F54A mutant of SEQ ID NO. 20. A mutant for the helix region of p53 was an F19A/L22A/W23A/L26A mutant of SEQ ID NO. 21.

NIH-3T3 cells were transfected using a FuGene 6 transfection reagent (Roche) with 500 ng of a pG5luc reporter plasmid, 500 ng of a p53 TAD plasmid, and 25 ng of a pCMV-LacZ plasmid. The cells were cultured for 48 hrs and collected. Then, luciferase activity and β-galactosidase activity were measured for each mutant using a luciferase assay system (Promega) and a β-galactosidase assay system (Promega).

EXAMPLE 7

Evaluation of the Inducing Effects of the p53 Turn-Derived Fragment Peptides on Apoptosis of Cancer Cells Carcinoma cell lines, MCF-7, HCT 11 6, A549 and SNU-71, were cultured in RPMI 1640 medium supplemented with 10% FBS and 100 U/ml penicillin/streptomycin in a humidified 5% $CO_2$ incubator (Gibco-BRL, UK) at 37° C. The cultured cancer cells were treated for 18 hrs with HIV-1 Tat(48-60)-p53 TAD(50-54), an alanine-substituted peptide of SEQ ID NO. 7 and a trytophane-substituted peptide of SEQ ID NO. 11. Then, induction of apoptosis of cancer cells was determined by an MTT assay using the tetrazolium salt, 3-(4,5-dimethylthiazol-2-yl)-2,5-diphenyltetrazolium bromide (MTT). In the MTT assay, after the cancer cells were incubated for 2 hrs in RPMI 1640 medium supplemented with 10% FBS and 0.5 mg/ml MTT, the medium was removed, and 100 μl of DMSO was added.

EXAMPLE 8

Calculation of the Structure of a p53 Turn-Derived Fragment Peptide in Complex with the mdm2 Protein by Molecular Modeling For mdm2, a previously identified crystal structure (RCSB entry number 1YCR) was utilized. Based on the results of transferred NOE experiments, manual docking was carried out for the p53 TAD(49-54) fragment peptide of SEQ ID NO. 6 in the state of forming an α-helix structure, thereby obtaining the initial complex structure. Molecular dynamics simulation was performed using the DISCOVER program in the Insight II package, and the final structure of the p53 TAD (49-54) in complex with the mdm2 protein was then calculated from this simulation.

The results of the above Examples are as follows.

8-1) Chemical Shift Perturbation Experiment for p53 TAD

Figure 2:
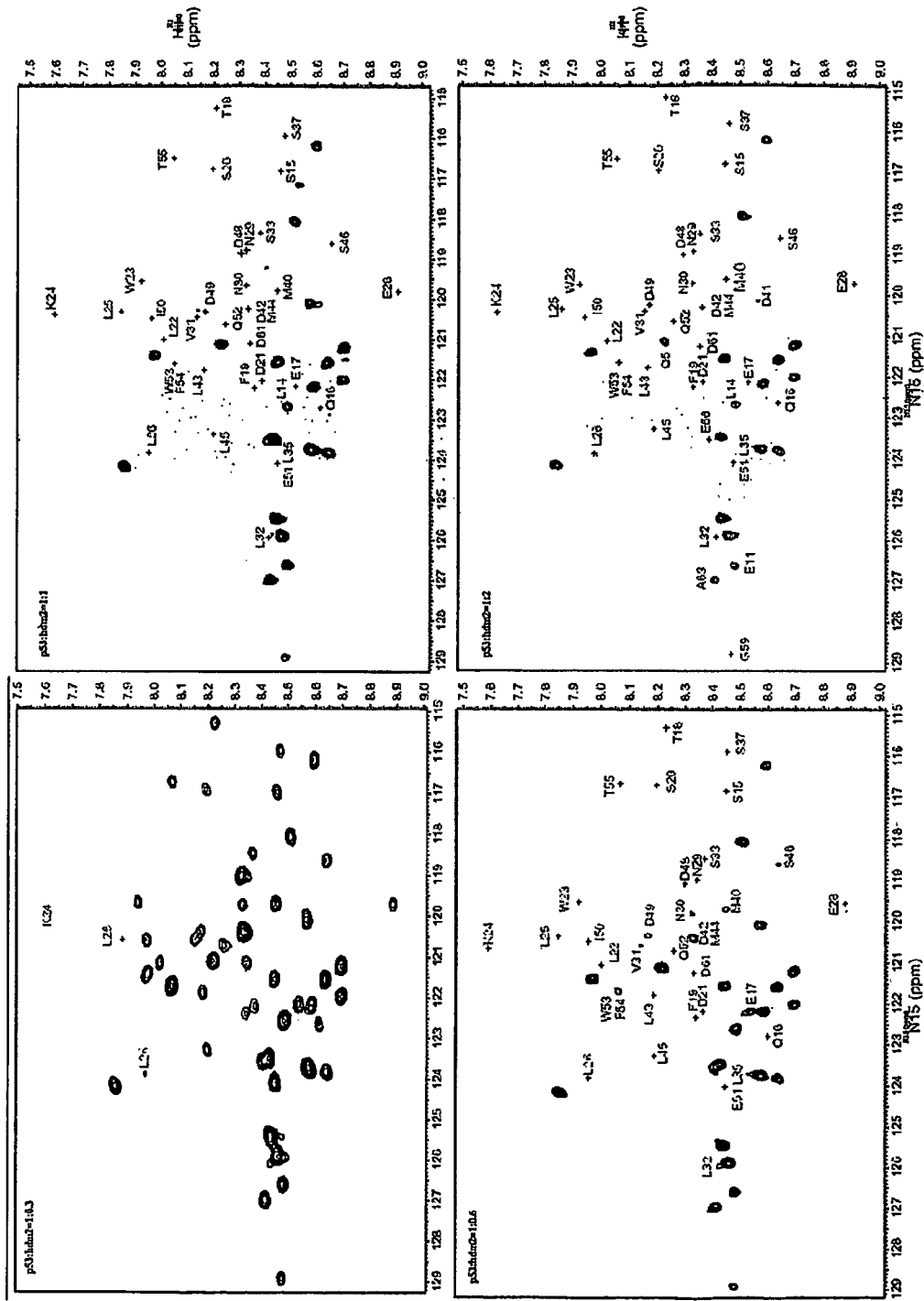
FIG. 2 shows $^{15}$N—$^{1}$H HSQC spectra of $^{15}$N-p53 TAD(1-73) in a bound state collected during titration of $^{15}$N-p53 TAD(1-73) with mdm2 (3-109) at $^{15}$N-p53 TAD(1-73): mdm2(3-109) molar ratios of 1:0.3, 1:0.6, 1:1 and 1:2.

As shown in FIG. 1, 2D $^{15}N-^1H$ HSQC spectra were collected for the free (unbound) form of purified $^{15}N$-labeled p53 TAD(1-73). Then, the $^{15}N$-p53 TAD(1-73) protein was titrated with increasing amounts of the mdm2(3-109) protein, and, during the titration, $^{15}N-^1H$ HSQC spectra of the bound form of $^{15}N$-p53 TAD(1-73) were collected (FIG. 2). During the titration, NMR peaks corresponding to 40 of 73 residues disappeared as $^{15}N$-p53 TAD(1-73) bound to mdm2(3-109). This is due to increased line widths of NMR peaks by chemical exchange between signals in a free state and signals in a bound state during the titration. Among the disappeared peaks, peaks corresponding to Lys24, Leu25 and Leu26 in the helix-forming region (Thr18-Leu26) of p53 disappeared first at the $^{15}N$-p53 TAD(1-73):mdm2(3-109) molar ratio of 1:0.3. At the next molar ratio of 1:0.6, NMR peaks corresponding to the remaining residues of the helix-forming region (indicated in red in FIG. 1) and the turn-forming region (Met40-Met44 and Asp48-Trp53) disappeared (indicated in green in FIG. 1). At the molar ratio of 1:1, NMR peaks for all residues of the helix and the turns disappeared, and, at molar ratios exceeding 1:1, no large changes were observed. These results are summarized in FIG. 3, indicating that the turns as well as the helix of p53 TAD participate in the binding to mdm2.

8-2) Chemical Shift Perturbation Experiment for mdm2 (3-109)

Figure 4:
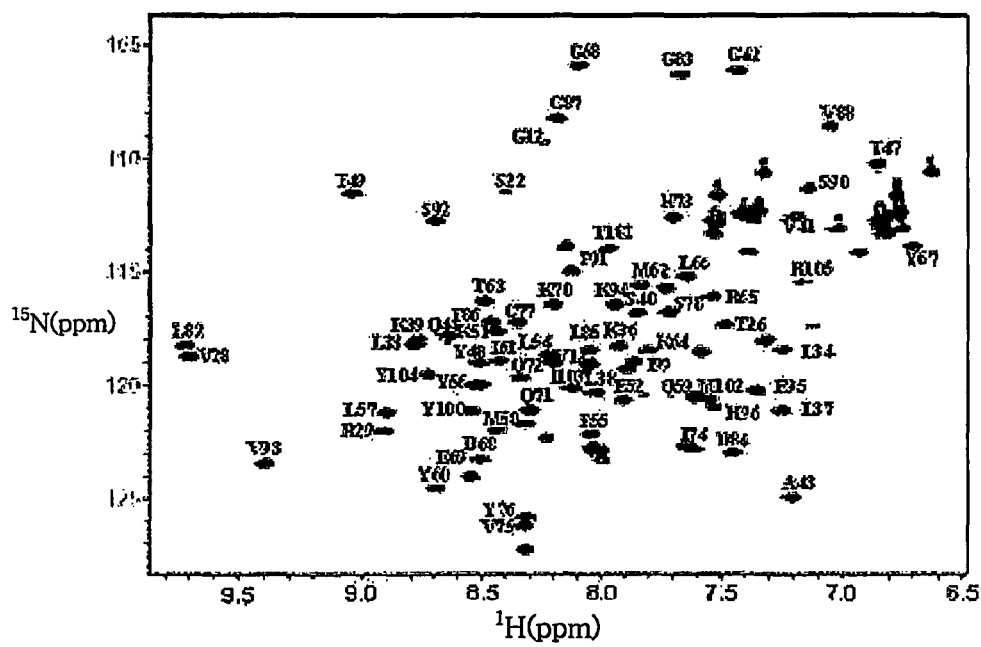
FIG. 4 is a $^{15}$N—$^1$H HSQC spectrum of $^{15}$N-mdm2(3-109) in a free state recorded at 0.2 mM of $^{15}$N-mdm2(3-109) and 25° C. Peaks from residues with assigned chemical shifts are labeled.
Figure 5:
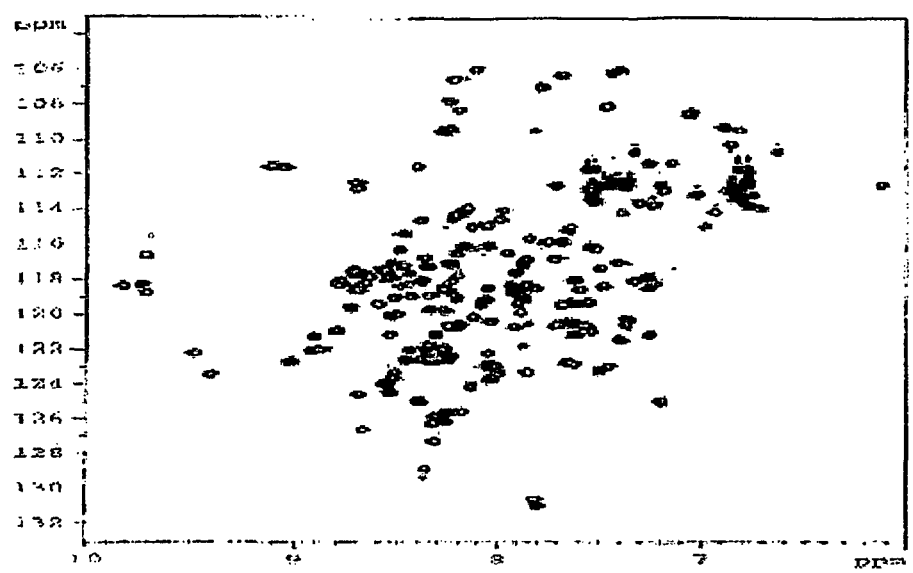
FIG. 5 is an overlaid view of two $^{15}$N—$^1$H HSQC spectra of $^{15}$N-mdm2(3-109) in a free state and in complex with p53 TAD(1-73), both of which have been recorded at 0.2 mM of $^{15}$N-mdm2(3-109) and 25° C. The spectrum of $^{15}$N-mdm2(3-109) in a free state is indicated in black, and the spectrum of $^{15}$N-mdm2 (3-109) in a bound state recorded at a $^{15}$N-mdm2(3-109):p53 TAD(1-73) molar ratio of 1:1 is indicated in red. The x and y axes of the spectra indicate chemical shifts (unit: ppm) of $^1$H and $^{15}$N, respectively.
Figure 6:
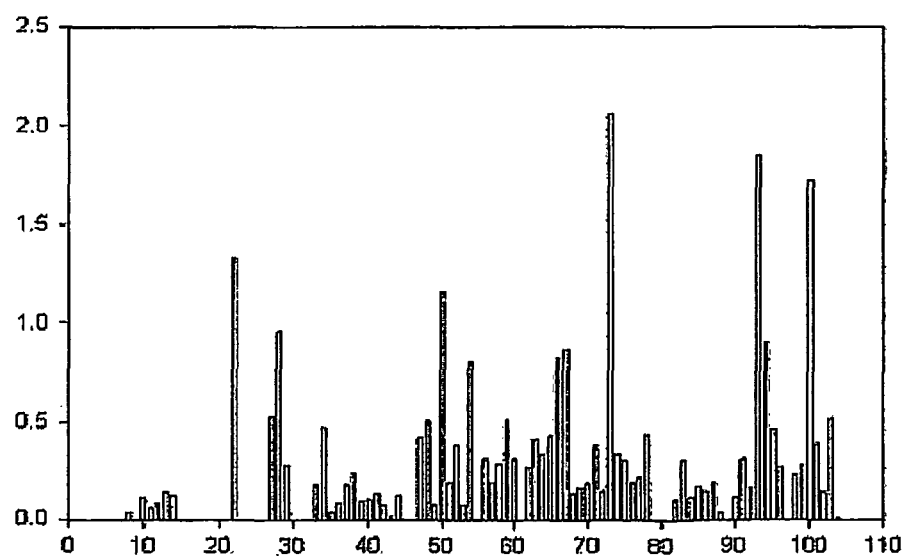
FIG. 6 is a graph showing changes in chemical shift calculated from the difference in chemical shift of $^{15}$N-mdm2 (3-109) in complex with p53 TAD(1-73), wherein the changes are calculated from the difference in chemical shift according to a known formula (Stoll, R. et al. (2001) Biochemistry 40, 336-344). The x axis represents amino acid resides of the mdm2 protein, and the y axis represents changes in chemical shift.

In contrast to the above 8-1), in order to identify the mdm2-binding site of the p53 TAD, $^{15}N$-labeled mdm2(3-109) was purified and titrated with p53 TAD(1-73) while 2D $^{15}N-^1H$ HSQC spectra were collected. First, HSQC spectra of $^{15}N$-mdm2(3-109) in a free state were collected (FIG. 4). Then, $^{15}N-^1H$ HSQC spectra of $^{15}N$-mdm2(3-109) in a bound state were collected during titration with p53 TAD(1-73) (FIG. 5), displaying different NMR peaks in a free and bound states because p53 TAD(1-73) was bound to mdm2(3-109) with high affinity. At a molar ratio exceeding 1:1, only peaks corresponding to the bound state were observed. Chemical shift assignments of mdm2(3-109) in a free and bound states were performed using 3D NMR experiments, HNCA, HNCOCA, $^{15}N$-edited TOCSY and $^{15}N$-edited NOESY spectrum analysis. Changes calculated from chemical shifts (FIG. 6) were almost similar to previously reported chemical shift perturbations of the p53 α-helix (Stoli, R. et al. (2001) Biochemistry 40, 336-344). These results demonstrated that the mdm2-binding site of the p53 TAD(1-73) is identical to that of the p53 α-helix (FIG. 7).

Figure 8:
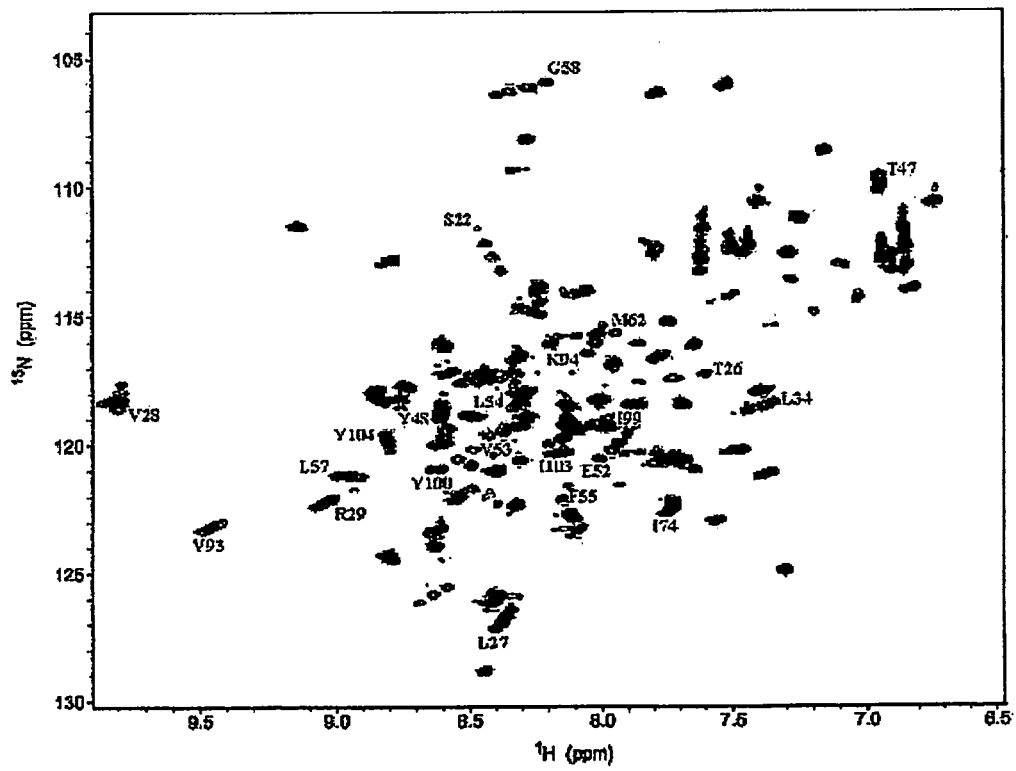
FIG. 8 shows $^{15}$N—$^1$H HSQC spectra of $^{15}$N-mdm2(3-109) in a bound state collected during titration of $^{15}$N-mdm2 (3-109) with p53 TAD(39-57) at 0.2 mM of $^{15}$N-mdm2(3-109) and 25° C., the three $^{15}$N—$^1$H HSQC spectra of $^{15}$N-mdm2(3-109) in a bound state collected while being titrated with p53 TAD(39-57) being overlaid with a spectrum of $^{15}$N-mdm2(3-109) in a free state. The spectrum of $^{15}$N-mdm2 (3-109) in a free state is indicated in black, and the spectra of $^{15}$N-mdm2(3-109) in a bound state collected $^{15}$N-mdm2(3-109):p53 TAD(39-57) molar ratios of 1:1, 1:2 and 1:3 are indicated in blue, pink and red, respectively.
Figure 9:
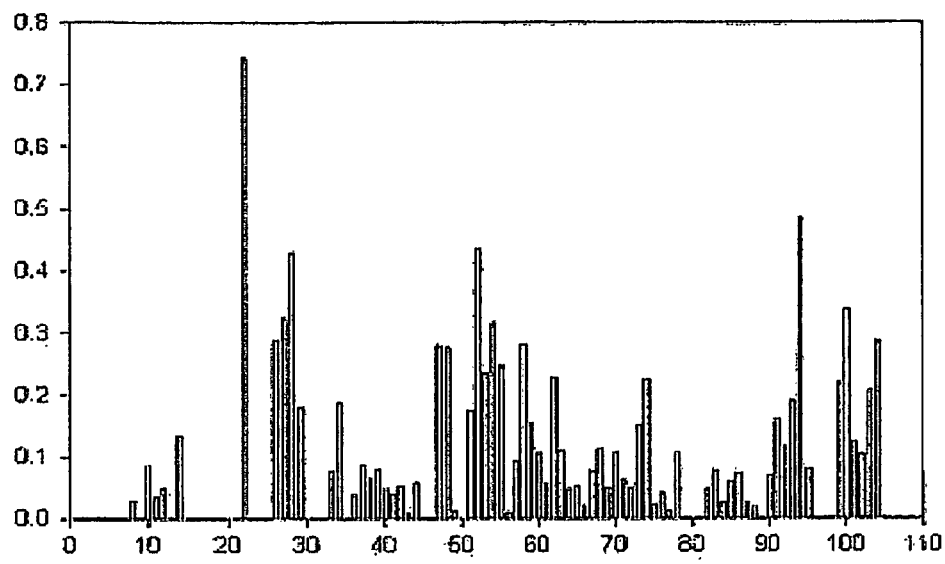
FIG. 9 is a graph showing changes in chemical shift calculated from the difference in chemical shift of $^{15}$N-mdm2(3-109) in complex with p53 TAD(39-57), wherein the changes are calculated from the difference in chemical shift according to the same method as in FIG. 6. The chemical shift of $^{15}$N-mdm2(3-109) in a bound state is measured at a $^{15}$N-mdm2 (3-109):p53 TAD(39-57) molar ratio of 1:3. The x axis represents amino acid resides of the mdm2 protein, and the y axis represents changes in chemical shift.
Figure 10:
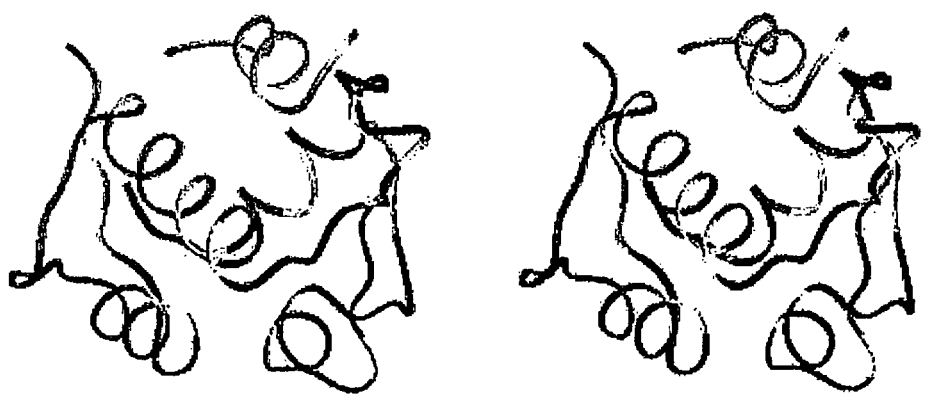
FIG. 10 is a stereo view in which residues with chemical shift changes calculated in FIG. 9 are represented in different colors in an X-ray crystal structure. Colors have the same meanings as in FIG. 7.

8-3) Chemical Shift Perturbation Experiment for p53 Turn-Derived Fragment Peptide 2D $^{15}N-^1H$ HSQC spectra were collected for the free (unbound) form of purified $^{15}N$-labeled mdm2(3-109). Then, the $^{15}N$-mdm2(3-109) was titrated with increasing amounts of p53 TAD(39-57), and, during the titration, $^{15}N-^1H$ HSQC spectra of the bound form of $^{15}N$-mdm2(3-109) were collected. Since the p53 TAD(39-57) was bound to the mdm2(3-109) with low affinity, NMR peaks in a free and bound states were balanced with each other by rapid chemical exchange, thus generating a single NMR peak. As shown in FIG. 8, in which a plurality of $^{15}N-^1H$ HSQC spectra obtained during the titration are overlaid, the average peak was found to continuously change during the titration. Chemical shift perturbations obtained from these changes in chemical shift were drawn as a graph (FIG. 9), and perturbed residues were distinguished from each other with different colors according to the extent of perturbation, thereby determining the mdm2-binding site on an X-ray crystal structure (FIG. 10).

Figure 7:
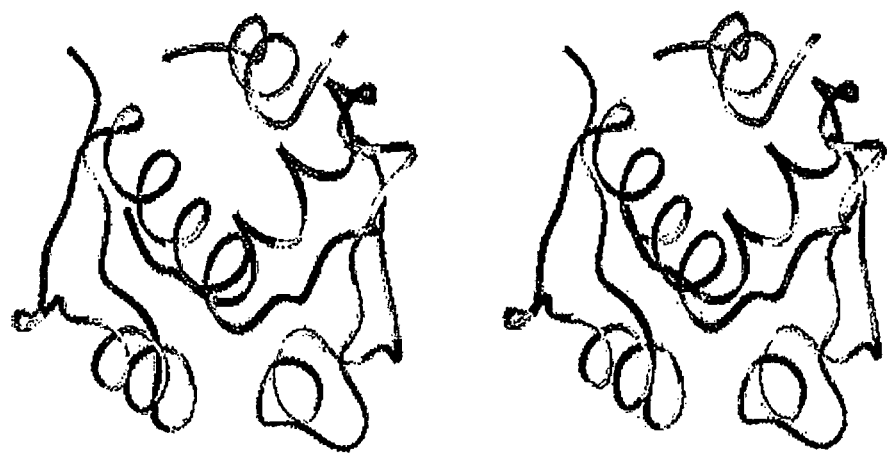
FIG. 7 is a stereoview in which residues with chemical shift changes calculated in FIG. 6 are represented in different colors in an X-ray crystal structure. The X-ray crystal structure of mdm2 is obtained from the Protein Data Bank (PDB) (PDB code: 1YCR) (Kussie, R. H. et al. (1996) Science 274, 948-953). In the crystal structure, the N-terminal end of the entire molecule is located in the left upper region. A p53 TAD fragment shown in the X-ray crystal structure encompasses the helix region of p53 (residues 15-29), and the N-terminal end of the helix is located at the right region. Changes in chemical shift are represented by ribbons, which are red for a change of more than 0.3, yellow for a change of 0.1-0.3, and blue for a change of less than 0.1.
Figure 11:
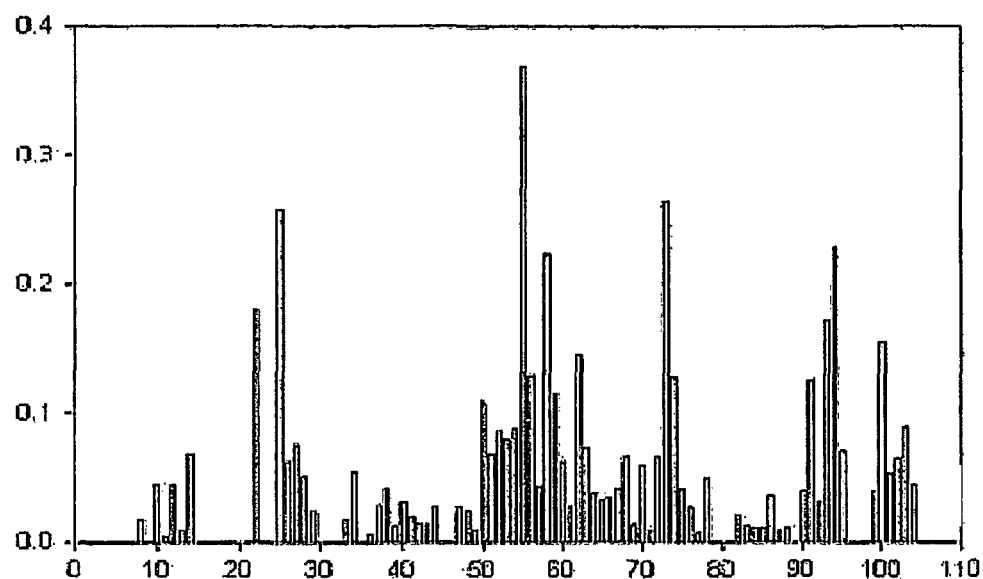
FIG. 11 is a graph showing changes in chemical shift calculated from the difference in chemical shift of $^{15}$N-mdm2 (3-109) in a bound state, measured after the addition of p53 TAD(49-54). A $^{15}$N—$^1$H HSQC spectrum has been collected at 0.2 mM of $^{15}$N-mdm2(3-109) and 25° C., and the chemical shift of $^{15}$N-mdm2(3-109) in a bound state is measured at a $^{15}$N-mdm2(3-109):p53 TAD(49-54) molar ratio of 1:6. The x axis represents amino acid resides of the $^{15}$N-mdm2 protein, and the y axis represents changes in chemical shift.
Figure 12:
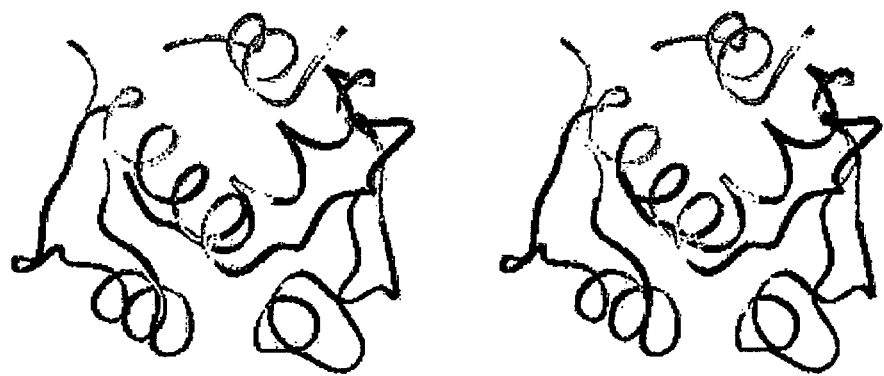
FIG. 12 is a stereoview in which residues with chemical shift changes calculated in FIG. 11 are represented in different colors in an X-ray crystal structure. Colors have the same meanings as in FIG. 7.

A comparison of these results with the results given in FIG. 7 revealed that the mdm2-binding site of p53 TAD(1-73) is almost identical to that of the p53 helix. p53 fragment peptides, including the native p53 TAD(49-54) peptide of SEQ ID NO. 6 (FIGS. 11 and 12), the Ala-substituted peptide of SEQ ID NO. 7 relative to the native p53 TAD(49-54) peptide (FIG. 13), the native p53 TAD(39-48) peptide of SEQ ID NO. 8 (FIG. 14), the native p53 TAD(49-57) peptide of SEQ ID NO. 9 (FIG. 15), the Ala-substituted peptide of SEQ ID NO. 10 relative to the native p53 TAD(49-57) peptide (FIG. 16), the Trp-substituted peptide of SEQ ID NO. 11 relative to the native p53 TAD(49-54) peptide (FIG. 17), and the Val-substituted peptide of SEQ ID NO. 12 relative to the native p53 TAD(49-54) peptide (FIG. 18), chemical shift perturbation experiments were carried out according to the same method as described above.

Figure 13:
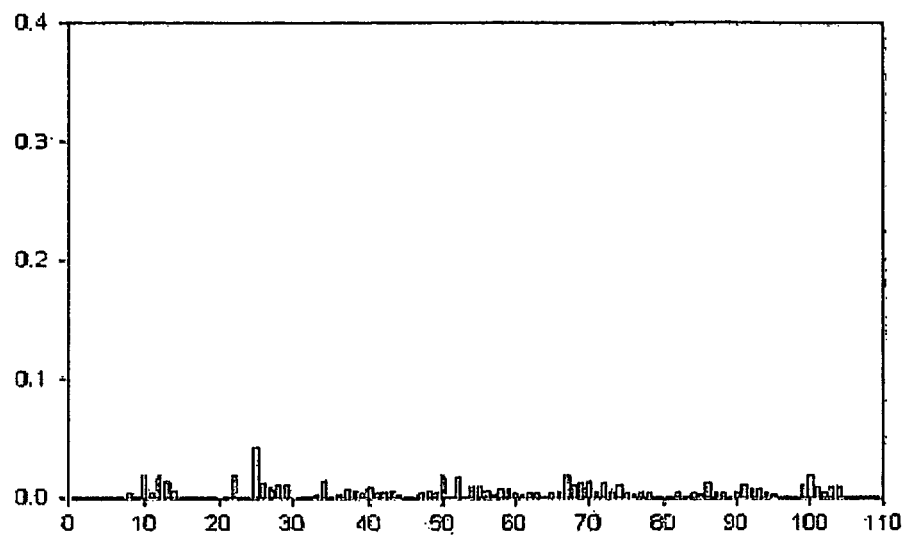
FIG. 13 is a graph showing changes in chemical shift calculated from the difference in chemical shift of $^{15}$N-mdm2 (3-109) in a bound state, measured after addition of an Ala-substituted peptide relative to p53 TAD(49-54). A $^{15}$N—$^1$H HSQC spectrum has been collected at 0.2 mM of $^{15}$N-mdm2 (3-109) and 25° C., and the chemical shift of $^{15}$N-mdm2(3-109) in a bound state is measured at a $^{15}$N-mdm2(3-109):Ala-substituted peptide of p53 TAD(49-54) molar ratio of 1:3. The x axis represents amino acid resides of the $^{15}$N-mdm2 protein, and the y axis represents changes in chemical shift.
Figure 14:
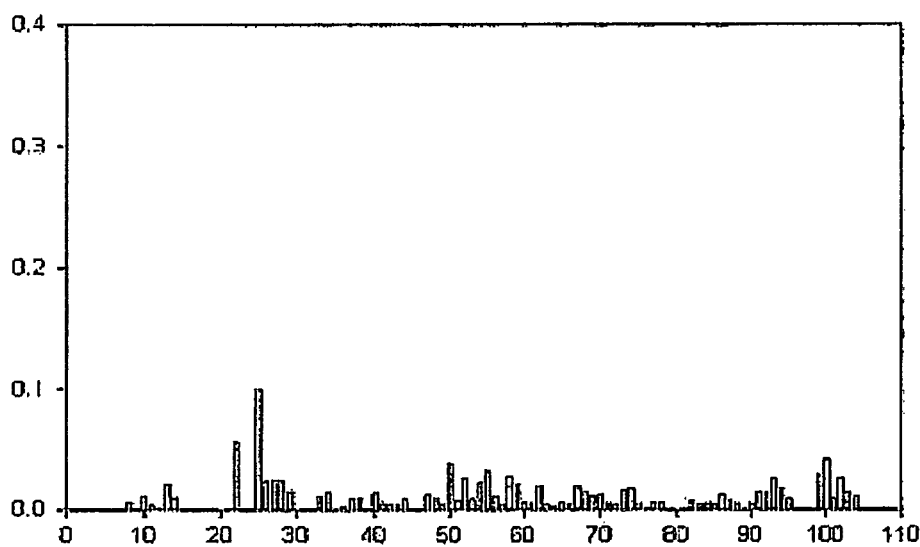
FIG. 14 is a graph showing changes in chemical shift calculated from the difference in chemical shift of $^{15}$N-mdm2 (3-109) in a bound state, measured after the addition of p53 TAD(39-48). A $^{15}$N—$^1$H HSQC spectrum has been collected at 0.2 mM of $^{15}$N-mdm2(3-109) and 25° C., and the chemical shift of $^{15}$N-mdm2(3-109) in a bound state is measured at a $^{15}$N-mdm2(3-109):p53 TAD(39-48) molar ratio of 1:3. The x axis represents amino acid resides of the $^{15}$N-mdm2 protein, and the y axis represents changes in chemical shift.
Figure 15:
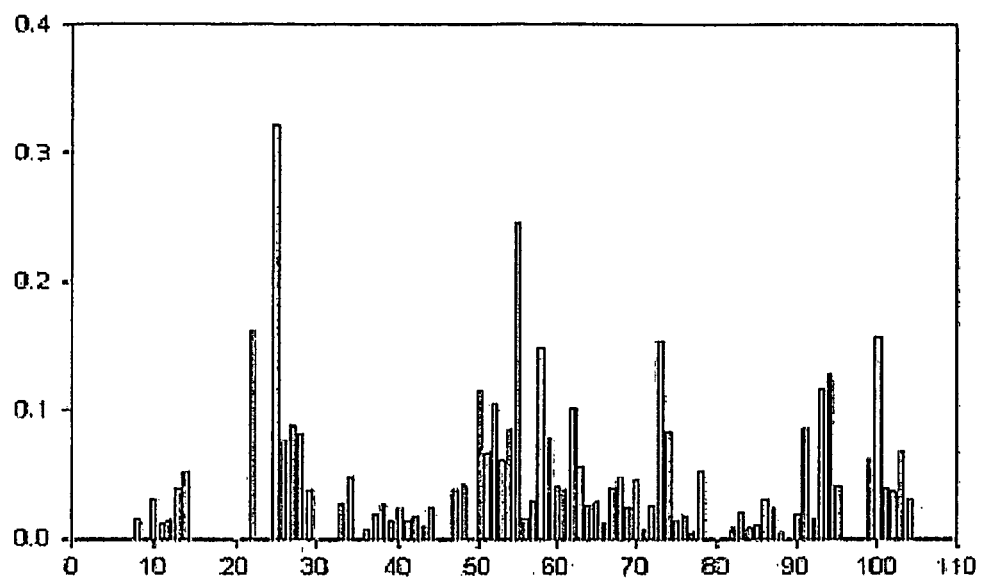
FIG. 15 is a graph showing changes in chemical shift calculated from the difference in chemical shift of $^{15}$N-mdm2 (3-109) in a bound state, measured after the addition of p53 TAD(49-57). A $^{15}$N—$^1$N HSQC spectrum has been collected at 0.2 mM of $^{15}$N-mdm2(3-109) and 25° C., and the chemical shift of $^{15}$N-mdm2(3-109) in a bound state is measured at a $^{15}$N-mdm2(3-109):p53 TAD(49-57) molar ratio of 1:6. The x axis represents amino acid resides of the $^{15}$N-mdm2 protein, and the y axis represents changes in chemical shift.
Figure 16:
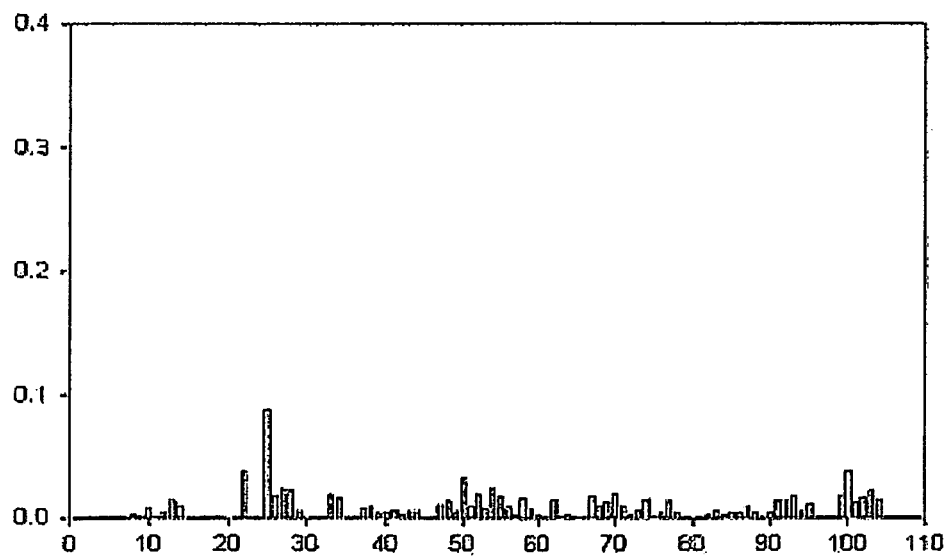
FIG. 16 is a graph showing changes in chemical shift calculated from the difference in chemical shift of $^{15}$N-mdm2 (3-109) in a bound state, measured after the addition of an Ala-substituted peptide relative to p53 TAD(49-57). A $^{15}$N—$^1$H HSQC spectrum has been collected at 0.2 mM of $^{15}$N-mdm2(3-109) and 25° C., and the chemical shift of $^{15}$N-mdm2(3-109) in a bound state is measured at a $^{15}$N-mdm2 (3-109):Ala-substituted peptide of p53 TAD(49-57) molar ratio of 1:3. The x axis represents amino acid resides of the $^{15}$N-mdm2 protein, and the y axis represents changes in chemical shift.
Figure 17:
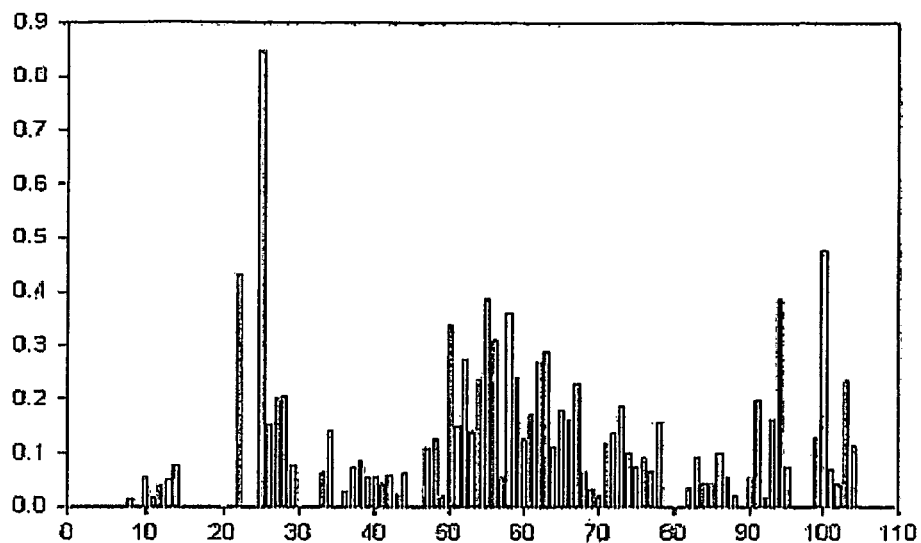
FIG. 17 is a graph showing changes in chemical shift calculated from the difference in chemical shift of $^{15}$N-mdm2 (3-109) in a bound state, measured after the addition of a Trp-substituted peptide relative to p53 TAD(49-54). A $^{15}$N—$^1$H HSQC spectrum has been collected at 0.2 mM, of $^{15}$N-mdm2(3-109) and 25° C., and the chemical shift of $^{15}$N-mdm2(3-109) in a bound state is measured at a $^{15}$N-mdm2 (3-109):Trp-substituted peptide of p53 TAD(49-54) molar ratio of 1:5.4. The x axis represents amino acid resides of the $^{15}$N-mdm2 protein, and the y axis represents changes in chemical shift.
Figure 18:
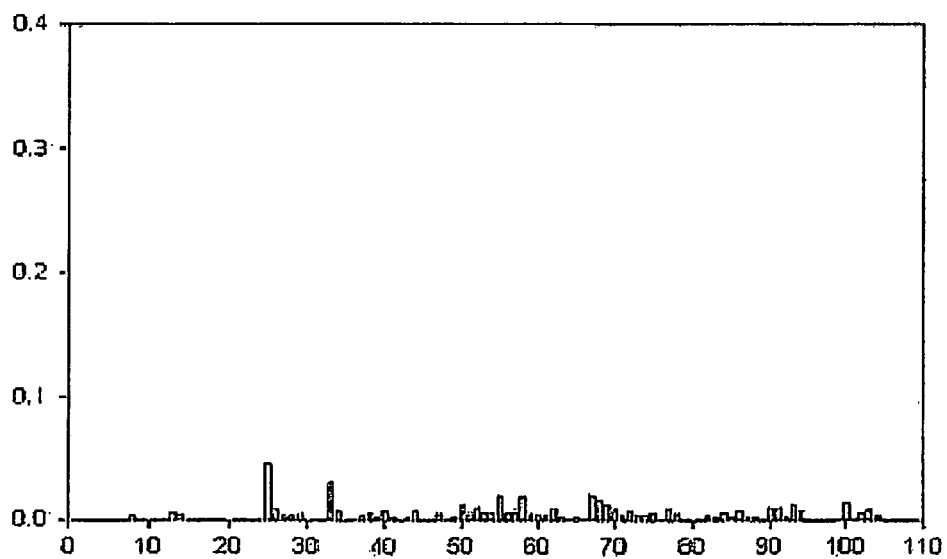
FIG. 18 is a graph showing changes in chemical shift calculated from the difference in chemical shift of $^{15}$N-mdm2 (3-109) in a bound state, measured after the addition of a Val-substituted peptide relative to p53 TAD(49-54). A $^{15}$N—$^1$H HSQC spectrum has been collected at 0.2 mM, of $^{15}$N-mdm2(3-109) and 25° C., and the chemical shift of $^{15}$N-mdm2(3-109) in a bound state is measured at a $^{15}$N-mdm2 (3-109):Val-substituted peptide of p53 TAD(49-54) molar ratio of 1:5.4. The x axis represents amino acid resides of the $^{15}$N-mdm2 protein, and the y axis represents changes in chemical shift.

As a result, the p53 TAD(49-54) and p53 TAD(49-57) peptides displayed chemical shift perturbation patterns similar to those of the p53 TAD(39-57) peptide (FIGS. 11 and 15), whereas the p53 TAD(39-48) peptide showed a small change in chemical shift (FIG. 14). These results demonstrate that the p53 TAD(49-54) peptide, the residues of which are located at the C-terminal end, is more critical for the binding to mdm2 than the p53 TAD(39-48) peptide, the residues of which are located at the N-terminal end. Also, the peptides, Ala-substituted for all of three hydrophobic residues (ILE50, Trp53, Phe54) predicted to be important for the binding to mdm2 relative to the native p53 TAD(49-54) and p53 TAD(49-57), showed remarkably decreased chemical shift changes, indicating that they do not bind to mdm2 (FIGS. 13 and 16). The peptide Trp-substituted for all of the three hydrophobic residues (ILE50, Trp53, Phe54) relative to the native p53 TAD (49-54) displayed much larger changes in chemical shift than the native p53 TAD(49-54) peptide (FIG. 17), indicating that it has high binding affinity for mdm2. In contrast, the peptide Val-substituted for all of the hydrophobic residues relative to the native p53 TAD(49-54) showed a small change in chemical shift, indicating that it has low binding affinity to mdm2 (FIG. 18).

8-4) BIAcore Experiments

Figure 19:
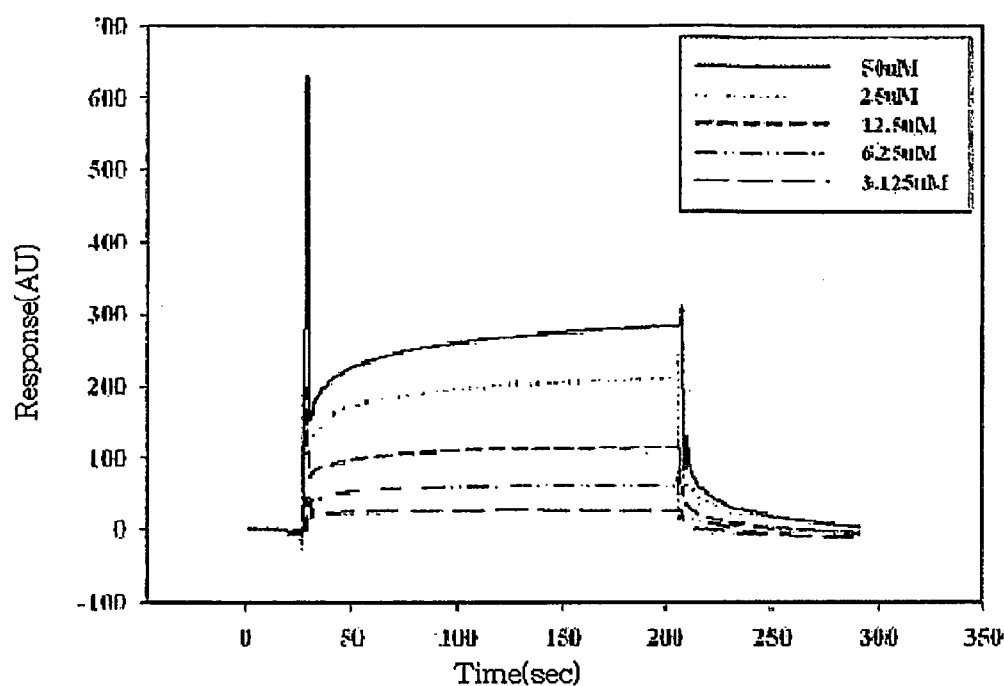
FIG. 19 is a sensorgram obtained from BIAcore experiments, which have been conducted at given time points during binding and dissociation between a mdm2(3-109) protein and a p53(49-54) peptide.

As shown in FIG. 19, which shows the sensorgrams obtained from BIAcore experiments, the p53(49-54) fragment peptide of SEQ ID NO. 6 bound specifically to the mdm2(3-109) protein. The dissociation equilibrium constant (Kd) measured from the sensorgram data was 25 μM.

8-5) Structural Analysis of p53 Turn-Derived Fragment Peptide

Figure 20:
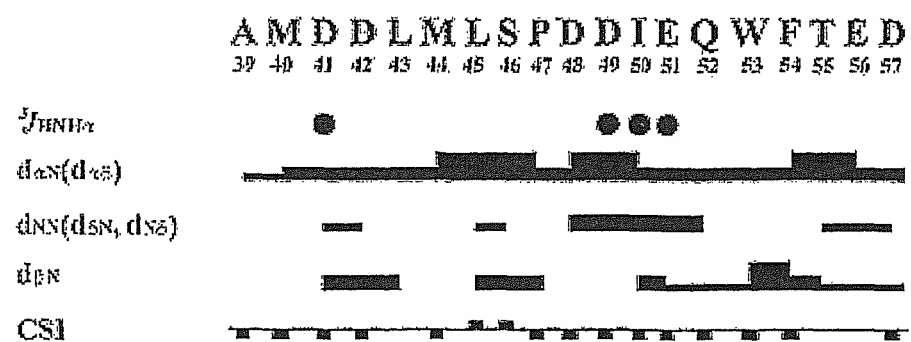
FIG. 20 is a view summarizing NOE patterns, $^3J_{HNH\alpha}$ coupling constants and chemical shift indices (CSI), observed in a NOESY spectrum of p53 TAD(39-57). This information has been deduced from two-dimensional (2D) NMR experiments carried out at 10° C. and 2 mM and in 80% methanol (pH 6.1).

Resonance assignments for NMR peaks of the p53 TAD (39-57) fragment peptide were carried out by analyzing 2D NMR spectra of TOCSY, NOESY and ROESY measured in 80% methanol, and distance information between hydrogen atoms was deducted from observed NOE peaks. The distance information between hydrogen atoms, $^3J_{HNH\alpha}$ coupling constants and chemical shift indices (CSI), summarized in FIG. 20, demonstrate that residues 49-51 of the p53 TAD(39-57) fragment peptide form a secondary structure such as an α-helix or a turn.

Figure 21:
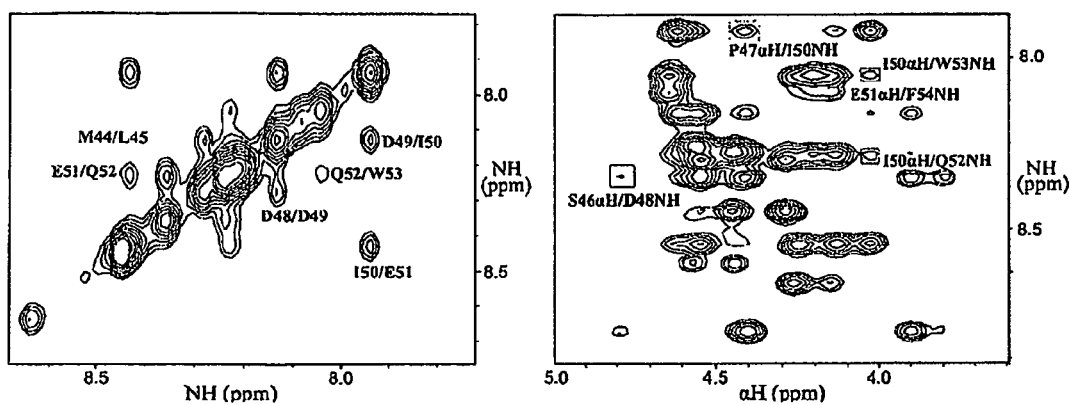
FIG. 21 shows TRNOE spectra of p53 TAD(39-57) bound to mdm2(3-109) recorded at a concentration ratio of 0.1 mM of mdm2(3-109) to 2 mM of p53 TAD(39-57), 10° C. and a mixing time of 100 ms, using a solvent consisting of 25 mM Tris-HCl (pH 7.5) and 150 mM NaCl. The left spectrum is the NH/NH region of NOESY, and the right spectrum is the NH/HA region of NOESY. NOEs demonstrating the helix structure are labeled with corresponding residues.
Figure 22:
FIG. 22 is a view summarizing NOE patterns observed in a TRNOE spectrum of p53 TAD(39-57) in complex with mdm2(3-109). The asterisk (*) indicates overlapping NMR peaks.

TRNOE experiments were carried out in order to determine the structure of the p53 TAD(39-57) bound to mdm2(3-109 in H$_2$O). The TRNOE spectra shown in FIG. 21 were recorded at a concentration ratio of 0.1 mM of mdm2(3-109) to 2 mM of p53 TAD(39-57), 10° C. and a mixing time of 100 ms, using a solvent consisting of 25 mM Tris-HCl (pH 7.5) and 150 mM NaCl. The NOE patterns shown in FIG. 22 demonstrate that residues 48-54 of p53 TAD(39-57) in the state bound to mdm2 (3-109) form the helix structure.

Figure 23:
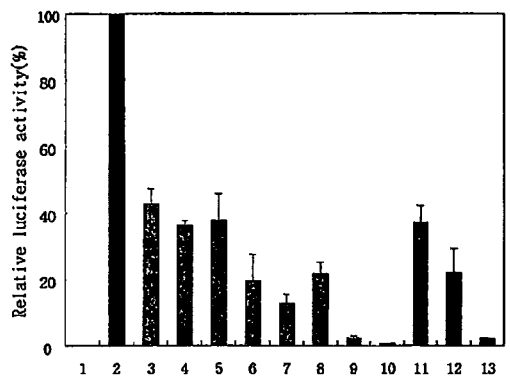
FIG. 23 shows the transcriptional activity of p53 TAD mutants. The transcriptional activity of β-galactosidase is used as a control, and luciferase activity relative to the wild-type p53 TAD is expressed as a percentage. Data are mean values of three independent experiments, and error bars represent standard deviation.

8-6) Evaluation of Transcription Activity of p53 TAD Mutants p53 TAD mutants, which were alanine substituted for hydrophobic residues present at the helix and turn regions of p53, were cloned, and their transcriptional activity was then measured and the results are given in FIG. 23. The transcriptional activity of β-galactosidase was used as a control, and luciferase activity relative to the wild-type p53 TAD was expressed as a percentage. As shown in FIG. 23, the mutants having alanine substitutions for residues in the turn regions as well as the helix region of p53 did not show the transcriptional activity of the p53 TAD. These results indicate that hydrophobic residues present in the turns play important roles in the p53 TAD function.

8-7) Evaluation of the Effects of the p53 Turn-Derived Fragment Peptides on Apoptosis Induction in Cancer Cells Four carcinoma cell lines were treated for 18 hrs with HIV-1 Tat(48-60)-p53 TAD(50-54), which was prepared by linking a cell permeable peptide HIV-1 Tat(48-60) consisting of amino acid residues 48-60 of the HIV-1 Tat protein of SEQ ID NO. 22 to the N-terminal end of p53 TAD(50-54), and alanine-substituted and trytophane-substituted peptides thereof. Then, the induction of apoptosis of cancer cells was determined by an MTT assay, and the cancer cells were microscopically observed. The alanine-substituted peptide showed a very low effect on apoptosis induction. In contrast, the p53 TAD(50-54) and the trytophane-substituted peptide displayed an IC$_{50}$ value of about 50 μM, indicating that they significantly induce apoptosis in cancer cells.

Figure 24:
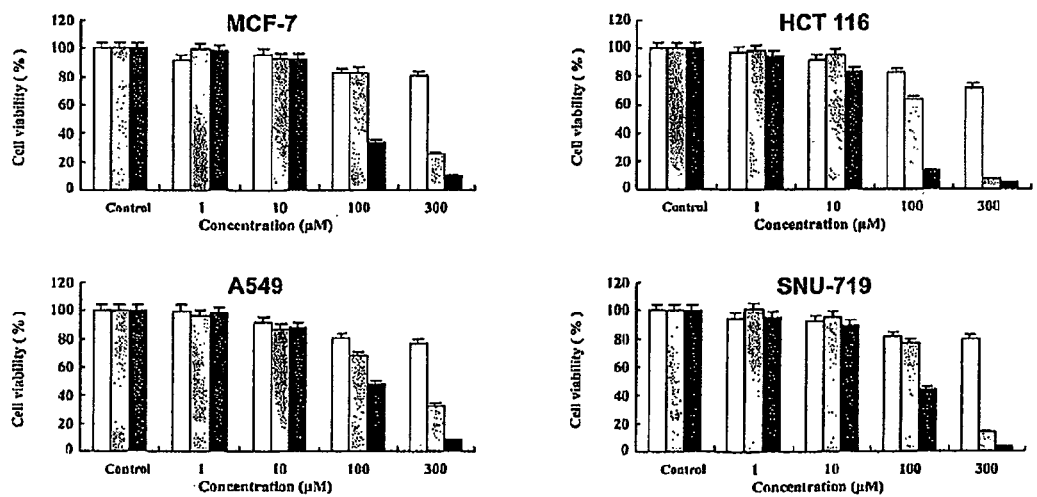
FIG. 24 shows the results of evaluation of the effects of p53 TAD(50-54) and its Trp-substituted peptide. The results of an MTT assay for p53 TAD(50-54) are represented by gray bars, and the MTT assay results for Ala- and Trp-substituted peptides are represented by white and black bars, respectively.
Figure 25:
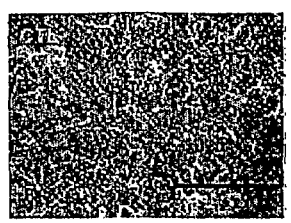
FIG. 25 shows microscopic photographs of MCF-7 cells treated with p53 TAD(50-54) and its Trp-substituted peptide. Middle panels show the cells treated with p53 TAD(50-54), and upper and lower panels show the cells treated with Ala- and Trp-substituted peptides, respectively (scale bar=100 μm>.
Figure 25:
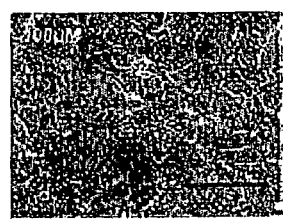
Figure 25:
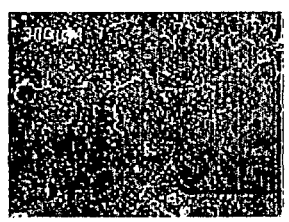
Figure 25:
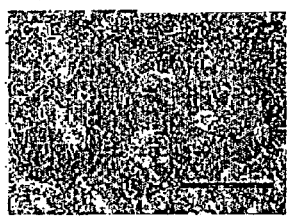
Figure 25:
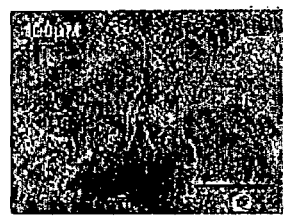
Figure 25:
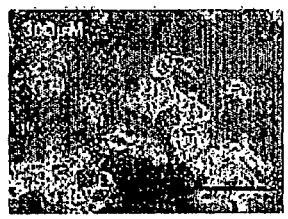
Figure 25:
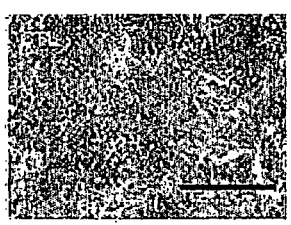
Figure 25:
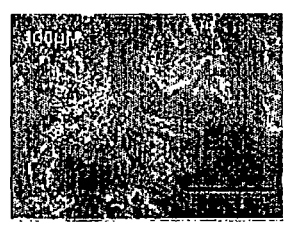
Figure 25:
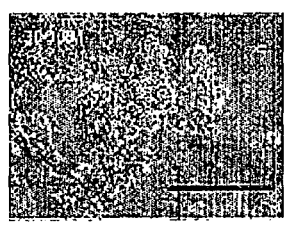
Figure 26:
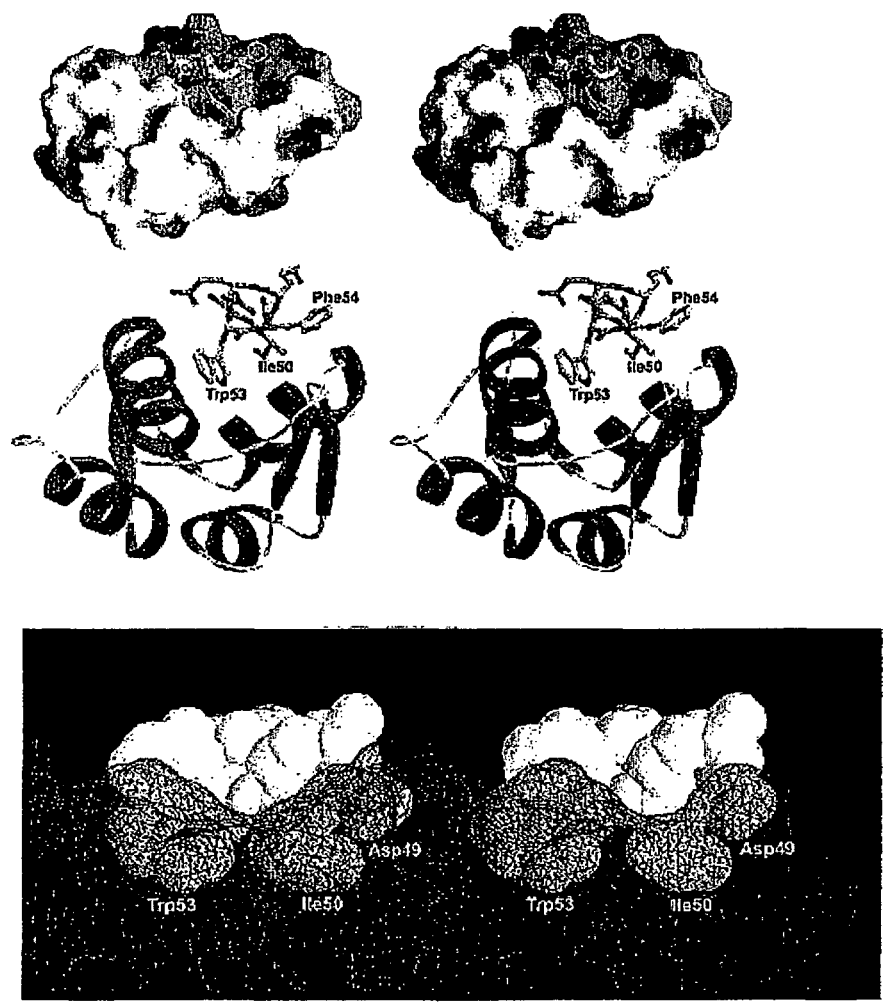
FIG. 26 shows the structure of a p53 TAD(49-54)-mdm2 protein complex. At the upper part, the electronic potential on mdm2, calculated by the GRASP program, is presented, and p53 TAD(49-54) is represented as a pink model. At the middle part, mdm2 is represented in a ribbon, and p53 TAD(49-54) as a green bar model. The mdm2-binding site is labeled with p53 residues forming hydrophobic interaction therewith. At the lower part, the intermolecular adjacent surface between mdm2 and p53 TAD(49-54) is indicated. Mdm2 is represented as a yellow CPK model, and its surface is expressed as a blue net. P53 residues complementarily binding to the mdm2-binding site are also indicated.

8-8) Calculation of the Structure of a p53 Turn-Derived Fragment Peptide in Complex with the mdm2 Protein by Molecular Modeling The structure of a p53 turn-derived fragment peptide in complex with the mdm2 protein was obtained by molecular dynamics simulation using the DISCOVER program (FIG. 26). For mdm2, a previously identified crystal structure (RCSB entry number 1YCR) was utilized. Based on the results of transferred NOE experiments, manual docking was carried out for the p53 TAD(49-54) fragment peptide in the state of forming a α-helix structure. As shown in FIG. 24, the hydrophobic residues of the p53 TAD(49-54) peptide, isoleucine at position 50, trytophane at position 53 and phenylalanine at position 54, formed complementary binding to the hydrophobic surface of the mdm2 protein-binding site.

INDUSTRIAL APPLICABILITY

The present peptides binding to the mdm2 protein effectively inhibit binding between p53 and mdm2 and induce apoptosis when administered to cancer cells or virus-infected cells. Therefore, the present peptides can be effectively used as therapeutic agents against cancer or viral infections, and are useful for designing and developing therapeutic agents against cancer or viral infections based on motifs of the peptide sequences.

The invention claimed is:

1. A method of inhibiting the complex formation of p53 and mdm2 (mouse double minute 2), comprising administering a peptide consisting of an amino acid sequence selected from the group consisting of DIEQWF (SEQ ID NO: 6) or DWEQWW (SEQ ID NO: 11), wherein the peptide specifically binds to the mdm2.

2. A method of inhibiting mdm2-mediated degradation, comprising administering a peptide consisting of an amino acid sequence selected from the group consisting of DIEQWF (SEQ ID NO: 6) or DWEQWW (SEQ ID NO: 11).

3. The method according to claim 2, comprising administering the peptide for an anticancer therapy to a subject in need thereof, wherein the anticancer therapy is for the treatment of leukemia, lymphomas, esophageal carcinomas, neuroblastoma or soft tissue tumors.

* * * * *